(12) United States Patent
Kellar et al.

(10) Patent No.: US 8,029,574 B2
(45) Date of Patent: Oct. 4, 2011

(54) PROSTHETIC KNEE JOINT

(75) Inventors: Franz W. Kellar, Gastonia, NC (US); Harold Lloyd Crowder, Concord, NC (US); Glenn A. Rupp, Cramerton, NC (US)

(73) Assignee: BioMedFlex LLC, Gastonia, NC (US)

( * ) Notice: Subject to any disclaimer, the term of this patent is extended or adjusted under 35 U.S.C. 154(b) by 0 days.

(21) Appl. No.: 12/983,191

(22) Filed: Dec. 31, 2010

(65) Prior Publication Data

US 2011/0087333 A1    Apr. 14, 2011

Related U.S. Application Data

(63) Continuation-in-part of application No. 12/826,620, filed on Jun. 29, 2010, now Pat. No. 7,914,580, which is a continuation-in-part of application No. 12/714,288, filed on Feb. 26, 2010, now Pat. No. 7,905,919, which is a continuation-in-part of application No. 11/936,601, filed on Nov. 7, 2007.

(60) Provisional application No. 60/864,667, filed on Nov. 7, 2006.

(51) Int. Cl.
*A61F 2/30* (2006.01)
*A61F 2/38* (2006.01)
*A61F 2/44* (2006.01)
*A61F 2/32* (2006.01)

(52) U.S. Cl. ............... 623/23.41; 623/18.11; 623/20.14; 623/20.15; 623/20.21; 623/20.22; 623/20.32; 623/23.39; 623/23.4; 623/23.43; 623/20.35

(58) Field of Classification Search ............... 623/14.12, 623/16.11, 18.11, 20.14–20.17, 20.21–20.36, 623/23.39–23.43
See application file for complete search history.

(56) References Cited

U.S. PATENT DOCUMENTS 3,521,302 A    7/1970    Muller
(Continued)

FOREIGN PATENT DOCUMENTS

DE    4102509    7/1992
(Continued)

OTHER PUBLICATIONS

Wenzel, S.A. and Shepherd, D.E.T., "Contact Stresses in Lumbar Total Disc Arthroplasty", vol. 17, No. 3, 2007, pp. 169-173, "Biomedical Materials and Engineering", Edgbaston, UK.

(Continued)

*Primary Examiner* — David Isabella
*Assistant Examiner* — Andrew Iwamaye
(74) *Attorney, Agent, or Firm* — Trego, Hines & Ladenheim, PLLC

(57) ABSTRACT

A prosthetic knee joint includes: (a) a femoral member comprising rigid material with a convex, wear-resistant femoral contact surface including a convex ridge; (b) a tibial assembly including: (i) at least one cup comprising rigid material with a body and a rim substantially thicker than the body defining a wear-resistant cup contact surface; (ii) a rigid base; and (iii) a spring support interconnecting the cup and the base, the spring support elastically deflectable permitting controlled pivoting of the at least one cup; (c) wherein the cup contact surface bears against the femoral contact surface, transferring axial and lateral loads between the cup and femoral member, while allowing pivoting between the cup and femoral member; and (d) wherein the at least one cup allows the rim to deform elastically, permitting the cup contact surface to conform in an irregular shape to the femoral contact surface, when the knee joint is loaded.

13 Claims, 34 Drawing Sheets

U.S. PATENT DOCUMENTS

| | | | |
|---|---|---|---|
| 3,723,995 A | 4/1973 | Baumann |
| 3,744,061 A | 7/1973 | Frost |
| 3,842,442 A | 10/1974 | Kolbel |
| 3,945,739 A | 3/1976 | Abe |
| 4,031,570 A | 6/1977 | Frey |
| 4,044,403 A | 8/1977 | D'Errico |
| 4,159,544 A | 7/1979 | Termanini |
| 4,224,696 A | 9/1980 | Murray et al. |
| 4,309,778 A | 1/1982 | Buechel et al. |
| 4,437,193 A | 3/1984 | Oh |
| 4,550,450 A | 11/1985 | Kinnett |
| 4,568,348 A | 2/1986 | Johnson et al. |
| 4,673,408 A | 6/1987 | Grobbelaar |
| 4,718,911 A | 1/1988 | Kenna |
| 4,759,766 A | 7/1988 | Buettner Janz et al. |
| 4,795,469 A | 1/1989 | Oh |
| 4,813,961 A | 3/1989 | Sostegni |
| 4,878,918 A | 11/1989 | Tari et al. |
| 4,904,106 A | 2/1990 | Love |
| 4,964,865 A | 10/1990 | Burkhead et al. |
| 4,997,432 A | 3/1991 | Keller |
| 5,061,288 A | 10/1991 | Berggren et al. |
| 5,062,853 A | 11/1991 | Forte |
| 5,080,675 A | 1/1992 | Lawes et al. |
| 5,080,678 A | 1/1992 | Spotorno et al. |
| 5,092,898 A | 3/1992 | Bekki et al. |
| 5,116,375 A | 5/1992 | Hofmann |
| 5,116,376 A | 5/1992 | May |
| 5,181,926 A | 1/1993 | Koch et al. |
| 5,197,987 A | 3/1993 | Koch et al. |
| 5,358,530 A | 10/1994 | Hodorek |
| 5,405,394 A | 4/1995 | Davidson |
| 5,413,604 A | 5/1995 | Hodge |
| 5,462,362 A | 10/1995 | Yuhta et al. |
| 5,480,442 A | 1/1996 | Bertagnoli |
| 5,480,446 A | 1/1996 | Goodfellow et al. |
| 5,507,816 A | 4/1996 | Bullivant |
| 5,549,693 A | 8/1996 | Roux et al. |
| 5,549,695 A | 8/1996 | Spotorno et al. |
| 5,549,697 A | 8/1996 | Caldarise |
| 5,549,699 A | 8/1996 | MacMahon et al. |
| 5,549,700 A | 8/1996 | Graham et al. |
| 5,593,445 A | 1/1997 | Waits |
| 5,609,645 A | 3/1997 | Vinciguerra |
| 5,641,323 A | 6/1997 | Caldarise |
| 5,674,296 A | 10/1997 | Bryan et al. |
| 5,676,701 A | 10/1997 | Yuan et al. |
| 5,702,456 A | 12/1997 | Pienkowski |
| 5,702,470 A | 12/1997 | Menon |
| 5,725,584 A | 3/1998 | Walker et al. |
| 5,782,927 A | 7/1998 | Klawitter et al. |
| 5,800,555 A | 9/1998 | Gray et al. |
| 5,824,101 A | 10/1998 | Pappas |
| 5,871,542 A | 2/1999 | Goodfellow et al. |
| 5,871,546 A | 2/1999 | Colleran et al. |
| 5,879,404 A | 3/1999 | Bateman et al. |
| 5,879,406 A | 3/1999 | Lilley |
| 5,893,889 A | 4/1999 | Harrington |
| 5,916,269 A | 6/1999 | Serbousek et al. |
| 5,935,174 A | 8/1999 | Dye |
| 5,938,702 A | 8/1999 | Lopez et al. |
| 5,955,919 A | 9/1999 | Lubbe et al. |
| 5,957,979 A | 9/1999 | Beckman et al. |
| 5,989,294 A | 11/1999 | Marlow |
| 5,997,579 A | 12/1999 | Albrektsson et al. |
| 6,013,103 A | 1/2000 | Kaufman et al. |
| 6,042,293 A | 3/2000 | Maughan |
| 6,059,830 A | 5/2000 | Lippincott, III et al. |
| 6,080,195 A | 6/2000 | Colleran et al. |
| 6,096,083 A | 8/2000 | Keller et al. |
| 6,126,695 A | 10/2000 | Semlitsch |
| 6,146,421 A | 11/2000 | Gordon et al. |
| 6,162,252 A | 12/2000 | Kuras et al. |
| 6,179,874 B1 | 1/2001 | Cauthen |
| 6,190,415 B1 | 2/2001 | Cooke et al. |
| 6,203,576 B1 | 3/2001 | Afriat et al. |
| 6,206,929 B1 | 3/2001 | Ochoa et al. |
| 6,217,249 B1 | 4/2001 | Merlo |
| 6,231,264 B1 | 5/2001 | McLaughlin et al. |
| 6,299,646 B1 | 10/2001 | Chambat et al. |
| 6,364,910 B1 | 4/2002 | Shultz et al. |
| 6,368,350 B1 | 4/2002 | Erickson et al. |
| 6,375,682 B1 | 4/2002 | Fleischmann et al. |
| 6,425,921 B1 | 7/2002 | Grundei et al. |
| 6,494,916 B1 | 12/2002 | Babalola et al. |
| 6,558,427 B2 | 5/2003 | Leclercq et al. |
| 6,660,040 B2 | 12/2003 | Chan et al. |
| RE38,409 E | 1/2004 | Noiles |
| 6,719,800 B2 | 4/2004 | Meyers et al. |
| 6,740,117 B2 | 5/2004 | Ralph et al. |
| 6,740,118 B2 | 5/2004 | Eisermann et al. |
| 6,743,258 B1 | 6/2004 | Keller |
| 6,770,095 B2 | 8/2004 | Grinberg et al. |
| 6,866,685 B2 | 3/2005 | Chan et al. |
| 6,875,235 B2 | 4/2005 | Ferree |
| 6,893,465 B2 | 5/2005 | Huang |
| 6,896,703 B2 | 5/2005 | Barbieri et al. |
| 6,942,701 B2 | 9/2005 | Taylor |
| 6,949,105 B2 | 9/2005 | Bryan et al. |
| 6,964,686 B2 | 11/2005 | Gordon |
| 6,972,039 B2 | 12/2005 | Metzger et al. |
| 6,981,989 B1 | 1/2006 | Fleischmann et al. |
| 6,981,991 B2 | 1/2006 | Ferree |
| 6,986,791 B1 | 1/2006 | Metzger |
| 7,001,433 B2 | 2/2006 | Songer et al. |
| 7,037,341 B2 | 5/2006 | Nowakowski |
| 7,060,099 B2 | 6/2006 | Carli et al. |
| 7,060,101 B2 | 6/2006 | O'Connor et al. |
| 7,066,963 B2 | 6/2006 | Naegerl |
| 7,083,650 B2 | 8/2006 | Moskowitz et al. |
| 7,083,651 B2 | 8/2006 | Diaz et al. |
| 7,083,652 B2 | 8/2006 | McCue et al. |
| 7,108,719 B2 | 9/2006 | Horber |
| 7,108,720 B2 | 9/2006 | Hanes |
| 7,121,755 B2 | 10/2006 | Schlapfer et al. |
| 7,153,325 B2 | 12/2006 | Kim et al. |
| 7,179,294 B2 | 2/2007 | Eisermann et al. |
| 7,214,243 B2 | 5/2007 | Taylor |
| 7,214,244 B2 | 5/2007 | Zubok et al. |
| 7,250,060 B2 | 7/2007 | Trieu |
| 7,270,679 B2 | 9/2007 | Istephanous et al. |
| 7,276,082 B2 | 10/2007 | Zdeblick et al. |
| 7,297,164 B2 | 11/2007 | Johnson et al. |
| 7,309,363 B2 | 12/2007 | Dietz |
| 7,326,250 B2 | 2/2008 | Beaurain et al. |
| 7,326,252 B2 | 2/2008 | Otto et al. |
| 7,338,529 B1 | 3/2008 | Higgins |
| 7,407,513 B2 | 8/2008 | Alleyne et al. |
| 7,442,211 B2 | 10/2008 | de Villiers et al. |
| 7,465,320 B1 | 12/2008 | Kito et al. |
| 7,468,076 B2 | 12/2008 | Zubok et al. |
| 7,468,079 B2 | 12/2008 | Collier |
| 7,470,287 B2 | 12/2008 | Tornier et al. |
| 7,485,145 B2 | 2/2009 | Purcell |
| 7,494,507 B2 | 2/2009 | Dixon et al. |
| 7,531,002 B2 | 5/2009 | Sutton et al. |
| 7,537,615 B2 | 5/2009 | Lemaire |
| 7,550,009 B2 | 6/2009 | Arnin et al. |
| 7,550,010 B2 | 6/2009 | Humphreys et al. |
| 7,572,295 B2 | 8/2009 | Steinberg |
| 7,572,296 B2 | 8/2009 | Scott et al. |
| 7,578,848 B2 | 8/2009 | Albert et al. |
| 7,582,115 B2 | 9/2009 | Weber |
| 7,588,384 B2 | 9/2009 | Yokohara |
| 7,611,653 B1 | 11/2009 | Elsner et al. |
| 7,618,439 B2 | 11/2009 | Zubok et al. |
| 7,618,459 B2 | 11/2009 | Justin et al. |
| 7,621,956 B2 | 11/2009 | Paul et al. |
| 7,655,041 B2 | 2/2010 | Clifford et al. |
| 7,658,767 B2 | 2/2010 | Wyss |
| 7,740,659 B2 | 6/2010 | Zarda et al. |
| 7,758,645 B2 | 7/2010 | Studer |
| 7,758,653 B2 | 7/2010 | Steinberg |
| 7,776,085 B2 | 8/2010 | Bernero et al. |
| 7,879,095 B2 | 2/2011 | Pisharodi |
| 7,905,919 B2 | 3/2011 | Kellar et al. |
| 2002/0111682 A1 | 8/2002 | Ralph et al. |

| Publication No. | Date | Inventor |
|---|---|---|
| 2002/0143402 A1 | 10/2002 | Steinberg |
| 2003/0055500 A1 | 3/2003 | Fell et al. |
| 2003/0081989 A1 | 5/2003 | Kondoh |
| 2003/0114935 A1 | 6/2003 | Chan et al. |
| 2003/0191534 A1 | 10/2003 | Viart et al. |
| 2003/0220691 A1 | 11/2003 | Songer et al. |
| 2004/0010316 A1 | 1/2004 | William et al. |
| 2004/0024460 A1 | 2/2004 | Ferree |
| 2004/0034433 A1 | 2/2004 | Chan et al. |
| 2004/0073311 A1 | 4/2004 | Ferree |
| 2004/0088052 A1 | 5/2004 | Dearnaley |
| 2004/0093087 A1 | 5/2004 | Ferree et al. |
| 2004/0117021 A1 | 6/2004 | Biedermann et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0167629 A1 | 8/2004 | Geremakis et al. |
| 2004/0172021 A1 | 9/2004 | Khalili |
| 2004/0215345 A1 | 10/2004 | Perrone, Jr. et al. |
| 2004/0220674 A1 | 11/2004 | Pria et al. |
| 2004/0260396 A1 | 12/2004 | Ferree et al. |
| 2004/0267374 A1 | 12/2004 | Friedrichs |
| 2004/0267375 A1 | 12/2004 | Friedrichs |
| 2005/0004572 A1 | 1/2005 | Biedermann et al. |
| 2005/0015152 A1 | 1/2005 | Sweeney |
| 2005/0021145 A1 | 1/2005 | de Villiers et al. |
| 2005/0038516 A1 | 2/2005 | Spoonamore |
| 2005/0055101 A1 | 3/2005 | Sifneos |
| 2005/0071007 A1 | 3/2005 | Malek |
| 2005/0080488 A1 | 4/2005 | Schultz |
| 2005/0113926 A1 | 5/2005 | Zucherman et al. |
| 2005/0113931 A1 | 5/2005 | Horber |
| 2005/0125065 A1 | 6/2005 | Zucherman et al. |
| 2005/0143827 A1 | 6/2005 | Globerman et al. |
| 2005/0165485 A1 | 7/2005 | Trieu |
| 2005/0171604 A1 | 8/2005 | Michalow |
| 2005/0171614 A1 | 8/2005 | Bacon |
| 2005/0192674 A1 | 9/2005 | Ferree |
| 2005/0197706 A1 | 9/2005 | Hovorka et al. |
| 2005/0203626 A1 | 9/2005 | Sears et al. |
| 2005/0216081 A1 | 9/2005 | Taylor |
| 2005/0251261 A1 | 11/2005 | Peterman |
| 2005/0251262 A1 | 11/2005 | de Villiers et al. |
| 2005/0261776 A1 | 11/2005 | Taylor |
| 2006/0020342 A1 | 1/2006 | Ferree et al. |
| 2006/0025862 A1 | 2/2006 | Villiers et al. |
| 2006/0041314 A1 | 2/2006 | Millard |
| 2006/0064169 A1 | 3/2006 | Ferree |
| 2006/0085076 A1 | 4/2006 | Krishna et al. |
| 2006/0095135 A1 | 5/2006 | Kovacevic |
| 2006/0129240 A1 | 6/2006 | Lessar et al. |
| 2006/0136062 A1 | 6/2006 | DiNello et al. |
| 2006/0178744 A1 | 8/2006 | de Villiers et al. |
| 2006/0190079 A1 | 8/2006 | Istephanous et al. |
| 2006/0200247 A1 | 9/2006 | Charrois |
| 2006/0217809 A1 | 9/2006 | Albert et al. |
| 2006/0235527 A1 | 10/2006 | Buettner-Janz et al. |
| 2006/0241765 A1 | 10/2006 | Burn et al. |
| 2006/0241766 A1 | 10/2006 | Felton et al. |
| 2006/0259147 A1 | 11/2006 | Krishna et al. |
| 2006/0259148 A1 | 11/2006 | Bar-Ziv |
| 2006/0271200 A1 | 11/2006 | Greenlee |
| 2006/0293752 A1 | 12/2006 | Moumene et al. |
| 2007/0021837 A1 | 1/2007 | Ashman |
| 2007/0032875 A1 | 2/2007 | Blacklock et al. |
| 2007/0032877 A1 | 2/2007 | Whiteside |
| 2007/0050032 A1 | 3/2007 | Gittings et al. |
| 2007/0073405 A1 | 3/2007 | Verhulst et al. |
| 2007/0073410 A1 | 3/2007 | Raugel |
| 2007/0083267 A1 | 4/2007 | Miz et al. |
| 2007/0100447 A1 | 5/2007 | Steinberg |
| 2007/0100454 A1 | 5/2007 | Burgess et al. |
| 2007/0100456 A1 | 5/2007 | Dooris et al. |
| 2007/0106391 A1 | 5/2007 | Ronk |
| 2007/0118223 A1 | 5/2007 | Allard et al. |
| 2007/0123990 A1 | 5/2007 | Sharifi-Mehr |
| 2007/0156246 A1 | 7/2007 | Meswania et al. |
| 2007/0168037 A1 | 7/2007 | Posnick |
| 2007/0173936 A1 | 7/2007 | Hester et al. |
| 2007/0185578 A1 | 8/2007 | O'Neil et al. |
| 2007/0208427 A1 | 9/2007 | Davidson et al. |
| 2007/0213821 A1 | 9/2007 | Kwak et al. |
| 2007/0225806 A1 | 9/2007 | Squires et al. |
| 2007/0225810 A1 | 9/2007 | Colleran et al. |
| 2007/0225818 A1 | 9/2007 | Reubelt et al. |
| 2007/0233244 A1 | 10/2007 | Lopez et al. |
| 2007/0239276 A1 | 10/2007 | Squires et al. |
| 2008/0065211 A1 | 3/2008 | Albert et al. |
| 2008/0065216 A1 | 3/2008 | Hurlbert et al. |
| 2008/0071381 A1 | 3/2008 | Buscher et al. |
| 2008/0077137 A1 | 3/2008 | Balderston |
| 2008/0133017 A1 | 6/2008 | Beyar et al. |
| 2008/0154263 A1 | 6/2008 | Janowski et al. |
| 2008/0154369 A1 | 6/2008 | Barr et al. |
| 2008/0161924 A1 | 7/2008 | Viker |
| 2008/0161930 A1 | 7/2008 | Carls et al. |
| 2008/0195212 A1 | 8/2008 | Nguyen et al. |
| 2008/0215156 A1 | 9/2008 | Duggal et al. |
| 2008/0221689 A1 | 9/2008 | Chaput et al. |
| 2008/0221690 A1 | 9/2008 | Chaput et al. |
| 2008/0228276 A1 | 9/2008 | Mathews et al. |
| 2008/0228282 A1 | 9/2008 | Brodowski |
| 2008/0243253 A1 | 10/2008 | Levieux |
| 2008/0243262 A1 | 10/2008 | Lee |
| 2008/0243263 A1 | 10/2008 | Lee et al. |
| 2008/0300685 A1 | 12/2008 | Carls et al. |
| 2009/0005872 A1 | 1/2009 | Moumene et al. |
| 2009/0012619 A1 | 1/2009 | Cordaro et al. |
| 2009/0030521 A1 | 1/2009 | Lee et al. |
| 2009/0036992 A1 | 2/2009 | Tsakonas |
| 2009/0043391 A1 | 2/2009 | de Villiers et al. |
| 2009/0054986 A1 | 2/2009 | Cordaro et al. |
| 2009/0062920 A1 | 3/2009 | Tauber |
| 2009/0076614 A1 | 3/2009 | Arramon |
| 2009/0082867 A1 | 3/2009 | Sebastian Bueno et al. |
| 2009/0082873 A1 | 3/2009 | Hazebrouck et al. |
| 2009/0088865 A1 | 4/2009 | Brehm |
| 2009/0105758 A1 | 4/2009 | Gimbel et al. |
| 2009/0125111 A1 | 5/2009 | Copf, Jr. |
| 2009/0138090 A1 | 5/2009 | Hurlbert et al. |
| 2009/0157185 A1 | 6/2009 | Kim |
| 2009/0192616 A1 | 7/2009 | Zielinski |
| 2009/0192617 A1 | 7/2009 | Arramon et al. |
| 2009/0215111 A1 | 8/2009 | Veenstra et al. |
| 2009/0234458 A1 | 9/2009 | de Villiers et al. |
| 2009/0248161 A1 | 10/2009 | Theofilos et al. |
| 2009/0270986 A1 | 10/2009 | Christensen |
| 2009/0276051 A1 | 11/2009 | Arramon et al. |
| 2009/0281629 A1 | 11/2009 | Roebling et al. |
| 2009/0306784 A1 | 12/2009 | Blum |
| 2009/0306785 A1 | 12/2009 | Farrar et al. |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0004746 A1 | 1/2010 | Arramon |
| 2010/0030335 A1 | 2/2010 | Arramon |
| 2010/0063589 A1 | 3/2010 | Tepic |
| 2010/0063597 A1 | 3/2010 | Gradel |
| 2010/0100189 A1 | 4/2010 | Metzger |
| 2010/0100191 A1 | 4/2010 | May et al. |
| 2010/0161064 A1 | 6/2010 | Kellar et al. |
| 2010/0161072 A1 | 6/2010 | Drescher |
| 2010/0191342 A1 | 7/2010 | Byrd et al. |
| 2010/0262250 A1 | 10/2010 | Kellar et al. |
| 2010/0268340 A1 | 10/2010 | Capote et al. |
| 2010/0292794 A1 | 11/2010 | Metz-Stavenhagen |
| 2010/0331993 A1 | 12/2010 | Gradl |

FOREIGN PATENT DOCUMENTS

| | | |
|---|---|---|
| DE | 4423020 | 1/1996 |
| DE | 10164328 | 7/2003 |
| DE | 202008004709 | 7/2008 |
| EP | 46926 | 3/1982 |
| EP | 648478 | 4/1995 |
| EP | 0636353 | 12/1995 |
| EP | 1508315 | 2/2005 |

| | | |
|---|---|---|
| FR | 2750036 | 12/1997 |
| FR | 2805456 | 8/2001 |
| FR | 2897528 | 8/2007 |
| GB | 1322680 | 7/1973 |
| GB | 1417407 | 12/1975 |
| GB | 1528906 | 10/1978 |
| GB | 2191402 | 12/1987 |
| JP | 2004011782 | 1/2004 |
| JP | 2004169820 | 6/2004 |
| WO | 9523566 | 9/1995 |
| WO | 9604867 | 2/1996 |
| WO | 9716138 | 5/1997 |
| WO | 9738650 | 10/1997 |
| WO | 0023015 | 4/2000 |
| WO | 03049649 | 6/2003 |
| WO | 2004066882 | 8/2004 |
| WO | 2005039455 | 5/2005 |
| WO | 2006069465 | 7/2006 |
| WO | 2007087730 | 8/2007 |
| WO | 2008088777 | 7/2008 |
| WO | 2008094260 | 8/2008 |
| WO | 2009094477 | 7/2009 |
| WO | 2009105884 | 9/2009 |
| WO | 2009121450 | 10/2009 |
| WO | 2009126908 | 10/2009 |
| WO | 2010095125 | 8/2010 |
| WO | 2011011340 | 1/2011 |

OTHER PUBLICATIONS

Clewlow, J.P., Pylios, T. and Shepherd, D.E.T., "Soft Layer Bearing Joins for Spine Arthroplasty", vol. 29, No. 10, Dec. 2008, pp. 1981-1985, "Materials and Design", Edgabaston, UK.

Parea, Philippe E., Chana, Frank W., Bhattacharyab, Sanghita and Goelb, Vijay K., "Surface Slide Track Mapping of Implants for Total Disc Arthroplasty", vol. 42, No. 2, Jan. 19, 2009, pp. 131-139, "Journal of Biomechanics", [online] [retrieved Feb. 19, 2010].

Dooris, Andrew P., Goel, Vijay K., Todd, Dwight T., Grosland, Nicole M., Wilder, David G., "Load Sharing in a Lumbar Motion Segment Implanted with an Artificial Disc Under Combined Sagittal Plane Loading", BED-vol. 42, 1999, pp. 277-278, American Society of Mechanical Engineers, Iowa City, Iowa.

Post, Zachary D., Matar, Wadih Y., Van De Leur, Tim, Grossman, Eric L., Austin, Matthew S., "Mobile-Bearing Total Knee Arthroplasty", vol. 25, No. 6, 2010, pp. 998-1003, "Journal of Arthroplasty", Philadelphia, Pennsylvania.

Fregly, Benjamin, J., Bei, Yanhong, Sylvester, Mark E., "Experimental Evaluation of an Elastic Foundation Model to Predict Contact Pressures in Knee Replacements", vol. 36, No. 11, Nov. 2003, pp. 1659-1668, "Journal of Biomechanics", Gainesville, Florida.

Minns, R.J., Campbell, J., "The 'Sliding Meniscus' Knee Prosthesis: Design Concepts", vol. 8, No. 4, Oct. 1979, pp. 201-205, "Engineering in Medicine", London, England.

Strickland, M.A., Taylor, M., "In-Silico Wear Prediction for Knee Replacements—Methodology and Corroboration", vol. 42, No. 10, Jul. 2009, "Journal of Biomechanics", Southampton, United Kingdom.

Halloran, Jason P., Easley, Sarah K., Patrella, Anthony J., Rullkoetter, Paul J., "Comparison of Deformable and Elastic Foundation Finite Element Simulations for Predicting Knee Replacement Mechanics", vol. 127, No. 5, Oct. 2005, pp. 813-818, "Journal of Biomechanical Engineering", Denver, Colorado.

Guerinot, Alexandre, E., Magleby, Spencer, P. Howell, Larry L., "Preliminary Design Concepts for Compliant Mechanism Prosthetic Knee Joints", vol. 2B, pp. 1103-1111, 2004, "Proceedings of the ASME Design Engineering Technical Conference", Provo, Utah.

Walker, Peter, S., Sathasivam, Shivani, "The Design of Guide Surfaces for Fixed-Bearing and Mobile-Bearing Knee Replacements", vol. 32, No. 1, pp. 27-34, Jan. 1999, "Journal of Biomechanics", Middlesex, United Kingdom.

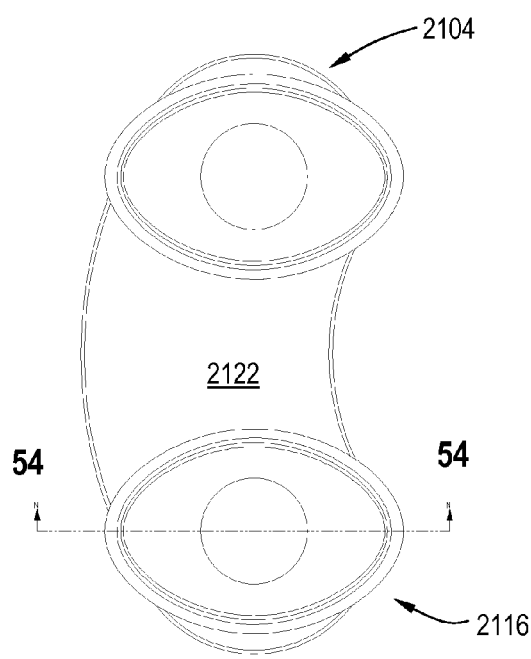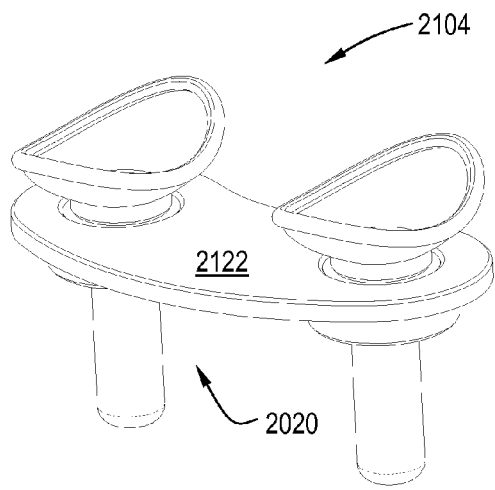
FIG. 52
FIG. 53
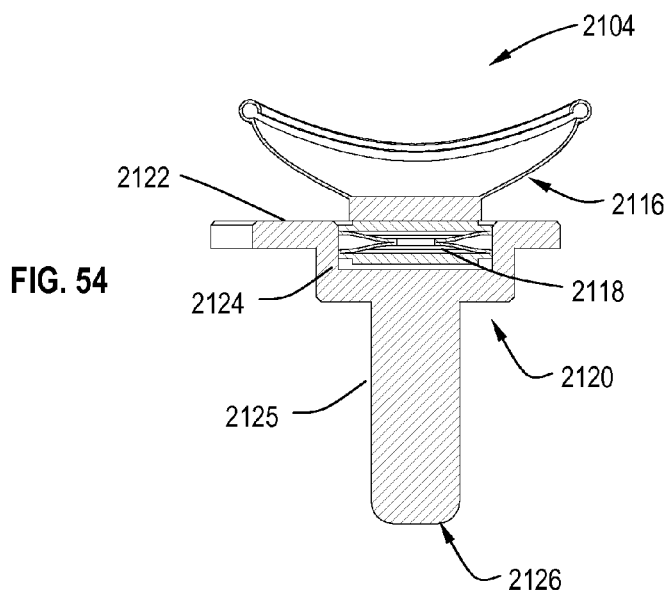
FIG. 54

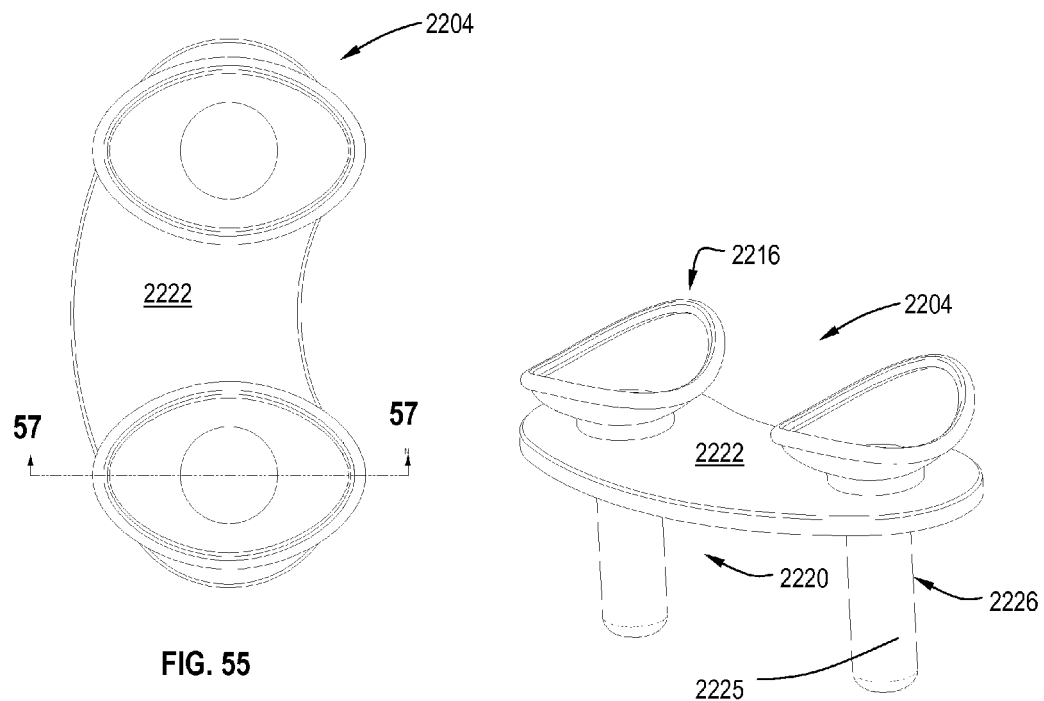
FIG. 55
FIG. 56
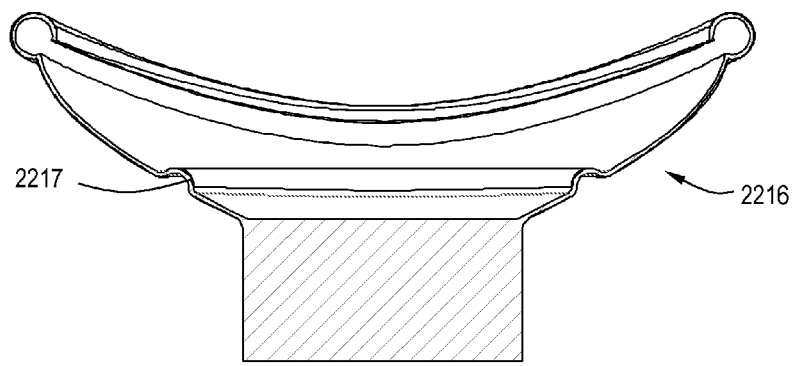
FIG. 57

PROSTHETIC KNEE JOINT

CROSS-REFERENCE TO RELATED APPLICATIONS

This application is a Continuation-in-Part of application Ser. No. 12/826,620, filed Jun. 29, 2010, currently pending, which is a Continuation-in-Part of application Ser. No. 12/714,288, filed Feb. 26, 2010, currently pending, which is a Continuation-in-Part of application Ser. No. 11/936,601, filed Nov. 7, 2007, currently pending. This application claims the benefit of Provisional Patent Application 60/864,667, filed on Nov. 7, 2006.

BACKGROUND OF THE INVENTION

This invention relates generally to medical implants, and more particularly to prosthetic joints having conformal geometries and wear resistant properties.

Medical implants, such as knee, hip, and spine orthopedic replacement joints and other joints and implants have previously consisted primarily of a hard metal motion element that engages a polymer contact pad. This has usually been a high density high wear resistant polymer, for example Ultra-High Molecular Weight Polyethylene (UHMWPE), or other resilient material. The problem with this type of configuration is the polymer eventually begins to degrade due to the caustic nature of blood, the high impact load, and high number of load cycles. As the resilient member degrades, pieces of polymer may be liberated into the joint area, often causing accelerated wear, implant damage, and tissue inflammation and harm.

It is desirable to employ a design using a hard member on a hard member (e.g. metals or ceramics), thus eliminating the polymer. Such a design is expected to have a longer service life. Extended implant life is important as it is now often required to revise or replace implants. Implant replacement is undesirable from a cost, inconvenience, patient health, and resource consumption standpoint.

Implants using two hard elements of conventional design will be, however, subject to rapid wear. First, a joint having one hard, rigid element on another will not be perfectly shaped to a nominal geometry. Such imperfections will result in points of high stress, thus causing localized wear. Furthermore, two hard elements would lack the resilient nature of a natural joint. Natural cartilage has a definite resilient property, absorbing shock and distributing periodic elevated loads. This in turn extends the life of a natural joint and reduces stress on neighboring support bone and tissue. If two rigid members are used, this ability to absorb the shock of an active lifestyle could be diminished. The rigid members would transmit the excessive shock to the implant to bone interface. Some cyclical load in these areas stimulates bone growth and strength; however, excessive loads or shock stress or impulse loading the bone-to-implant interface will result in localized bone mass loss, inflammation, and reduced support.

BRIEF SUMMARY OF THE INVENTION

These and other shortcomings of the prior art are addressed by the present invention, which provides a prosthetic joint having wear-resistant contacting surfaces with conformal properties.

According to one aspect of the invention a prosthetic knee joint includes: (a) a femoral member comprising a rigid material and having a convex-curved, wear-resistant femoral contact surface, the femoral contact surface including at least one protruding ridge having a convex cross-sectional shape; (b) a tibial assembly including: (i) at least one cup comprising a rigid material and having a body and a rim extending around an open periphery of the body, the rim being substantially thicker than the body and defining a wear-resistant cup contact surface; (ii) a rigid base; and (iii) a spring support interconnecting at least part of the at least one cup and the base, the spring support elastically deflectable so as to permit controlled pivoting motion of the at least one cup relative to the base; (c) wherein the cup contact surface bears directly against the femoral contact surface, so as to transfer axial and lateral loads between the cup and the femoral member, while allowing pivoting motion between the tibial assembly and the femoral member; and (d) wherein the at least one cup is shaped and sized so as to allow the rim to deform elastically and permit the cup contact surface to conform in an irregular shape to the femoral contact surface, when the knee joint is placed under a predetermined load.

BRIEF DESCRIPTION OF THE DRAWINGS

The invention may be best understood by reference to the following description taken in conjunction with the accompanying drawing figures in which:

FIG. 52 is a top view of an alternative tibial assembly;

FIG. 53 is a perspective view of the tibial assembly of FIG. 52;

FIG. 54 is a cross-sectional view taken along lines 54-54 of FIG. 51;

FIG. 55 is a top view of another alternative tibial assembly;

FIG. 56 is a perspective view of the tibial assembly of FIG. 55;

FIG. 57 is a cross-sectional view taken along lines 57-57 of FIG. 55;

DETAILED DESCRIPTION OF THE INVENTION

The present invention provides a specialized implant contact interface (implant geometry). In this geometry, an implanted joint includes two typically hard (i.e. metal or ceramic) members; however, at least one of the members is formed such that it has the characteristics of a resilient member, such as: the ability to absorb an impact load; the ability to absorb high cycle loading (high endurance limit); the ability to be self cleaning; and the ability to function as a hydrodynamic and/or hydrostatic bearing.

Generally, the contact resilient member is flexible enough to allow elastic deformation and avoid localized load increases, but not so flexible as to risk plastic deformation, cracking and failure. In particular, the resilient member is designed such that the stress levels therein will be below the high-cycle fatigue endurance limit. As an example, the resilient member might be only about 10% to about 20% as stiff as a comparable solid member. It is also possible to construct the resilient member geometry with a variable stiffness, i.e. having a low effective spring rate for small deflections and a higher rate as the deflections increase, to avoid failure under sudden heavy loads.

Figure 1:
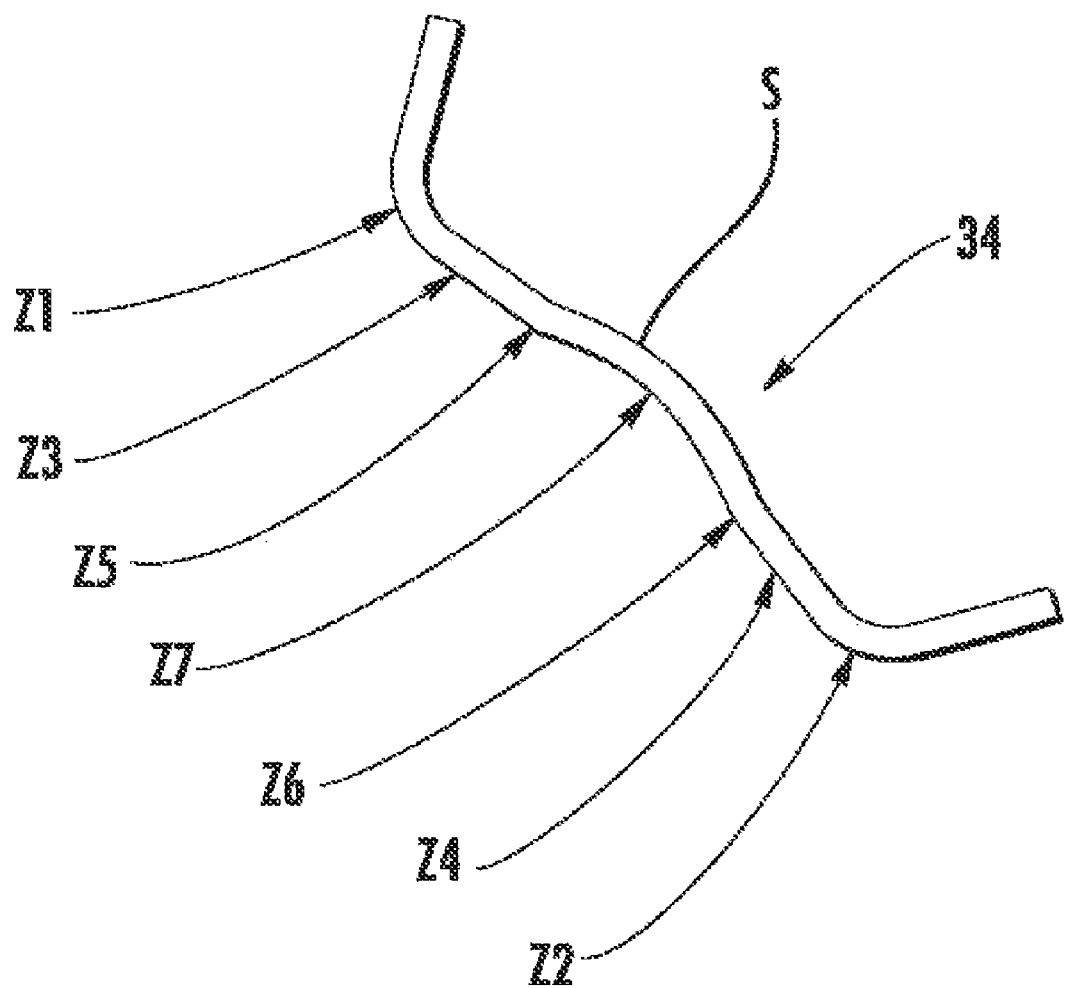
FIG. 1 is a cross-sectional view of a portion of a resilient contact member constructed in accordance with the present invention.

FIG. 1 illustrates an exemplary contact member 34 including a basic resilient interface geometry. The contact member 34 is representative of a portion of a medical implant and is made of one or more metals or ceramics (for example, partially stabilized Zirconia). It may be coated as described below. The geometry includes a lead-in shape, Z1 and Z2, a contact shape, Z3 and Z4, a lead-out shape, Z5 and Z6, and a relieved shape, Z7. It may be desired to vary the cross-sectional thickness to achieve a desired mechanical stiffness to substrate resilience characteristic. The presence of the relieved region Z7 introduces flexibility into the contact member 34, reduces the potential for concentrated point contact with a mating curved member, and provides a reservoir for a working fluid.

The Z7 region may be local to the contact member 34 or may be one of several. In any case, it may contain a means of providing fluid pressure to the internal contact cavity to produce a hydrostatic interface. A passive (powered by the regular motion of the patient) or active (powered by micro components and a dedicated subsystem) pumping means and optional filtration may be employed to provide the desired fluid interaction.

A hydrodynamic interface is desirable as, by definition, it means the contact member 34 is not actually touching the mating joint member. The lead-in and lead-out shapes Z1, Z2, Z5, Z6 are configured to generate a shear stress in the working fluid so as to create the fluid "wedge" of a hydrodynamic support.

Figure 2:
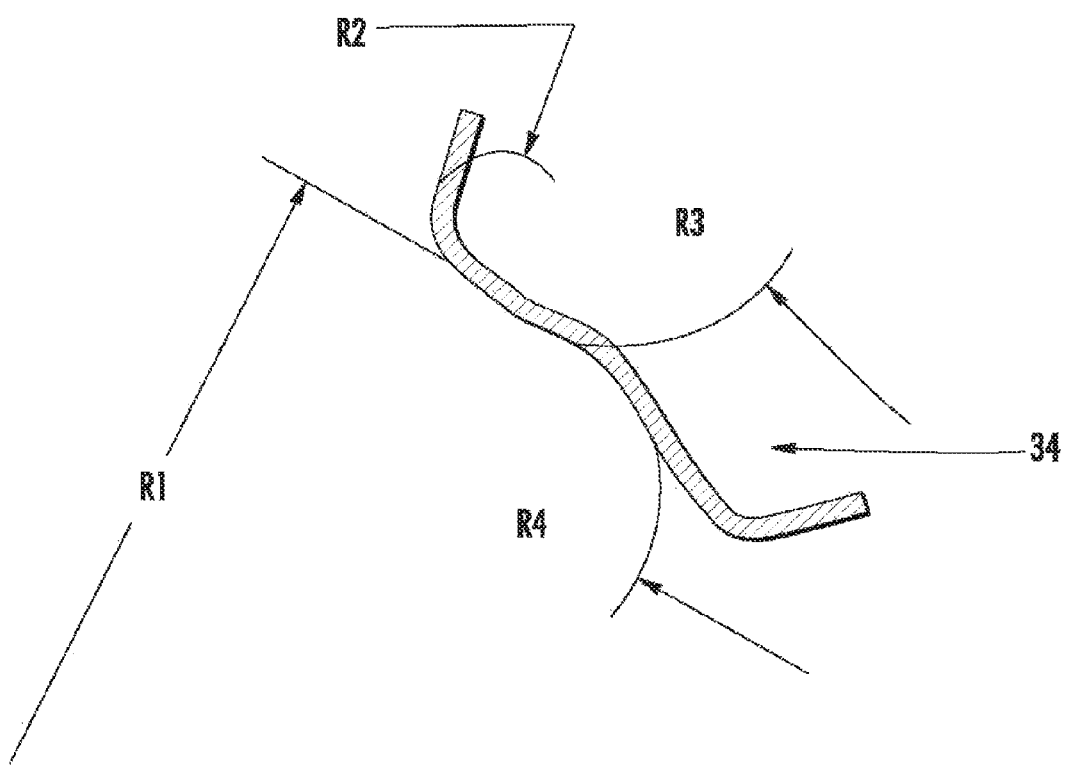
FIG. 2 is an enlarged view of the contact member of FIG. 1 in contact with a mating joint member.
Figure 3:
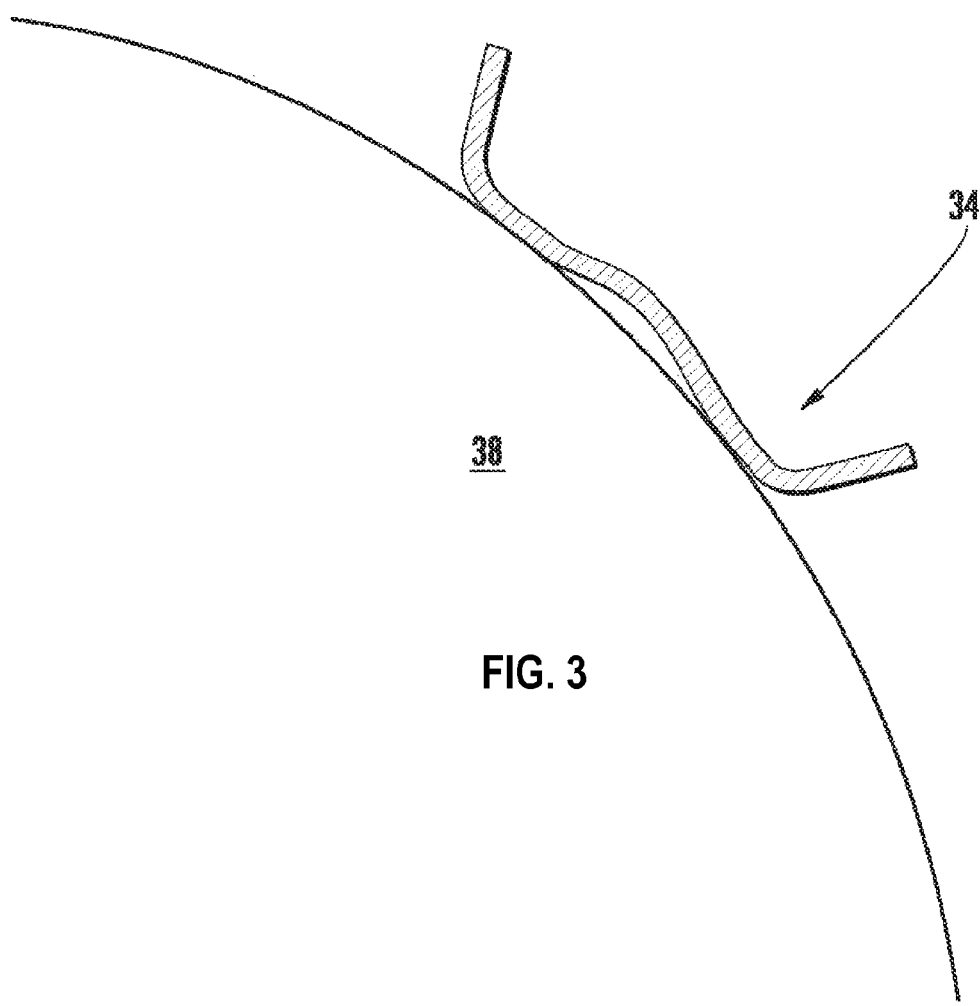
FIG. 3 is a side view of a resilient contact member in contact with a mating joint member.

FIG. 2 shows a closer view of the contact member 34. It may be desirable to make the contact radius (Z3 and Z4) larger or smaller, depending on the application requirement and flexural requirement. For example, FIG. 3 illustrates the contact member 34 in contact with a mating joint member 38 having a substantially larger radius than the contact member 34. The radius ratio between the two joint members is not particularly critical, so long as one of the members exhibits the resilient properties described herein.

The contact member 34 includes an osseointegration surface "S", which is a surface designed to be infiltrated by bone growth to improve the connection between the implant and the bone. Osseointegration surfaces may be made from materials such as TRABECULAR METAL, textured metal, or sintered or extruded implant integration textures. TRABECULAR METAL is an open metal structure with a high porosity (e.g. about 80%) and is available from Zimmer, Inc., Warsaw, Ind. 46580 USA.

Figure 4:
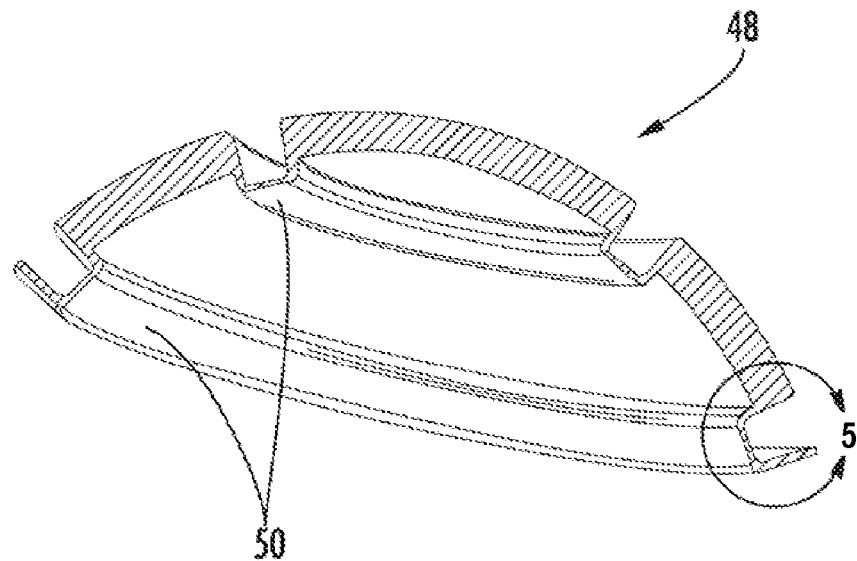
FIG. 4 is a cross-sectional view of a cup for an implant according to an alternate embodiment of the invention.
Figure 5:
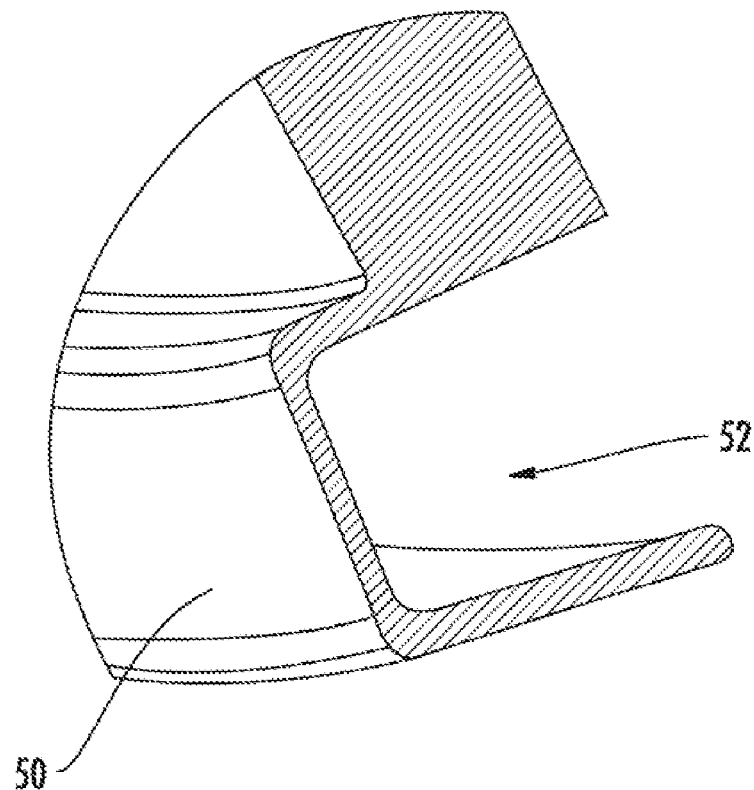
FIG. 5 is an enlarged view of a portion of the cup of FIG. 4.
Figure 6:
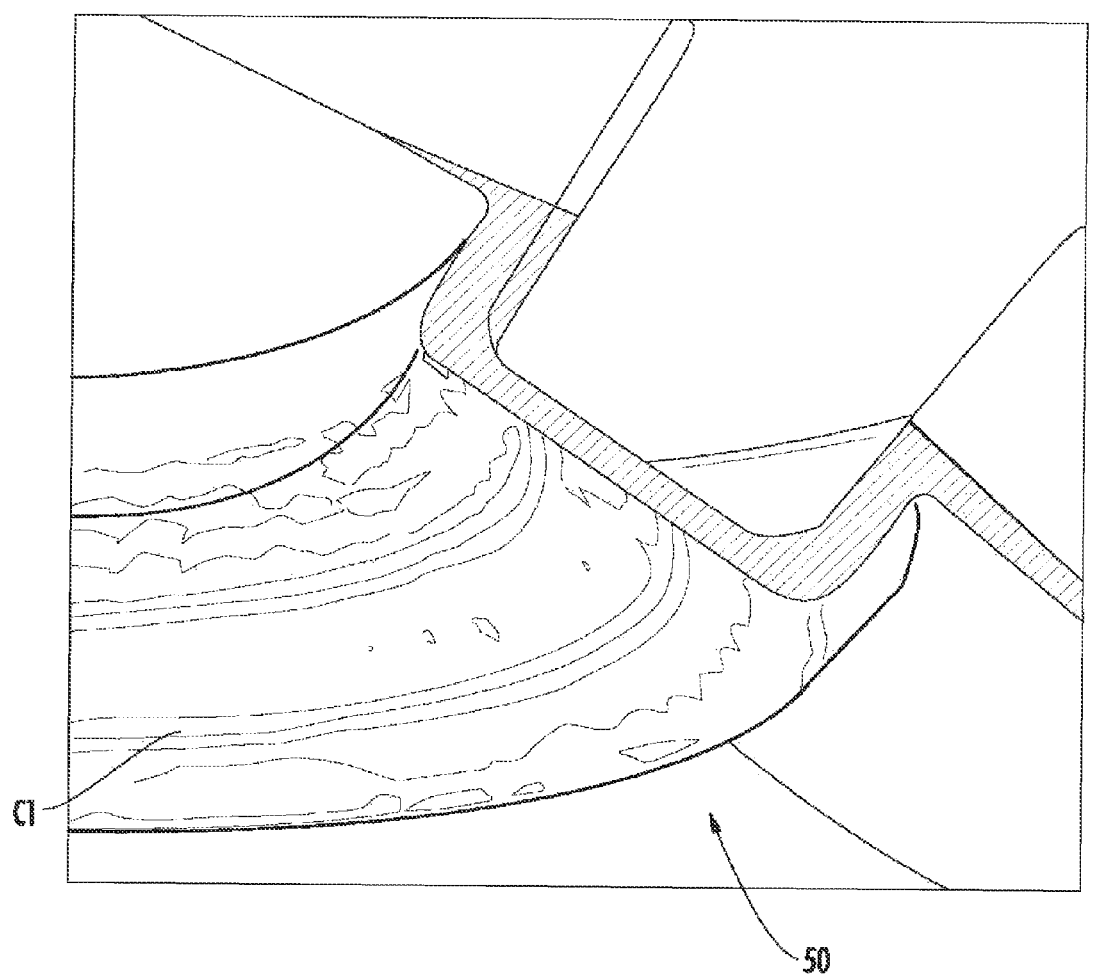
FIG. 6 is a perspective view of a finite element model of a joint member.

FIGS. 4 and 5 illustrate a cup 48 of metal or ceramic with two integrally-formed contact rings 50. More contact rings may be added if needed. As shown in FIG. 5, the volume behind the contact rings 50 may be relieved. This relieved area 52 may be shaped so as to produce a desired balance between resilience and stiffness. A varying cross-section geometry defined by varying inner and outer spline shapes may be desired. In other words, a constant thickness is not required. A material such as a gel or non-Newtonian fluid (not shown) may be disposed in the relieved area 52 to modify the stiffness and damping characteristics of the contact rings 50 as needed for a particular application. The cup 48 could be used as a stand-alone portion of a joint, or it could be positioned as a liner within a conventional liner. The contact ring 50 is shown under load in FIG. 6, which depicts contour lines of highest compressive stress at "C1". This is the portion of the contact ring 50 that would be expected to undergo bending first. The bearing interface portion of the resilient contact member could be constructed as a bridge cross-section supported on both sides as shown or as a cantilevered cross-section depending on the desired static and dynamic characteristics.

Figure 8:
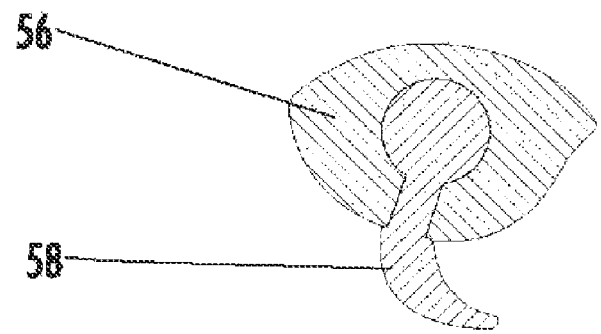
FIG. 8 is an enlarged view of a portion of FIG. 7.
Figure 7:
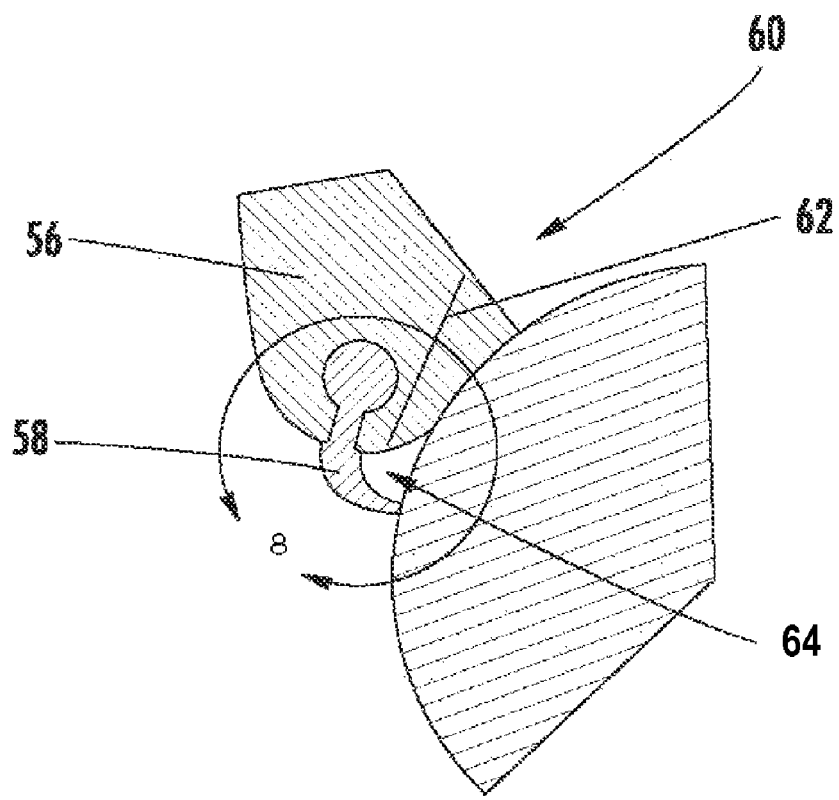
FIG. 7 is a cross-sectional view of an implant joint including a flexible seal.
Figure 9:
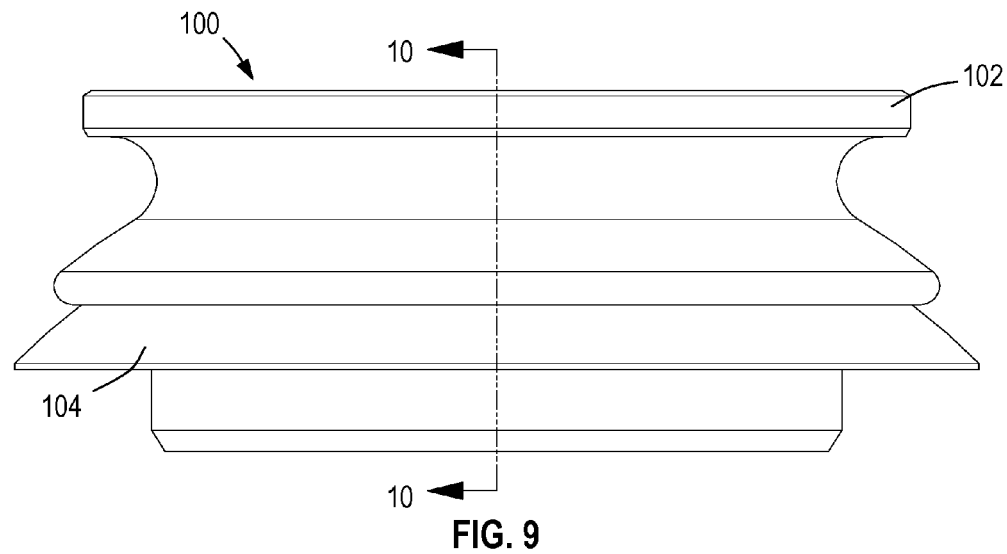
FIG. 9 is a side view of a prosthetic joint constructed in accordance with an aspect of the present invention.

FIGS. 7 and 8 illustrate an implant 56 of rigid material which includes a wiper seal 58. The wiper seal 58 keeps particles out of the contact area (seal void) 60 of the implant 58, and working fluid (natural or synthetic) in. The seal geometry is intended to be representative and a variety of seal characteristics may be employed; such as a single lip seal, a double or multiple lip seal, a pad or wiper seal made from a variety of material options. Different seal mounting options may be used, for example a lobe in a shaped groove as shown in FIGS. 7 and 8, a retaining ring or clamp, or an adhesive. The wiper seal 58 may also be integrated into the contact face of the interface zone.

It may be desirable to create a return passage 62 from the seal void region 60 back into the internal zone 64 in order to stabilize the pressure between the two and to allow for retention of the internal zone fluid if desired. This is especially relevant when the hydrostatic configuration is considered.

Figure 10:
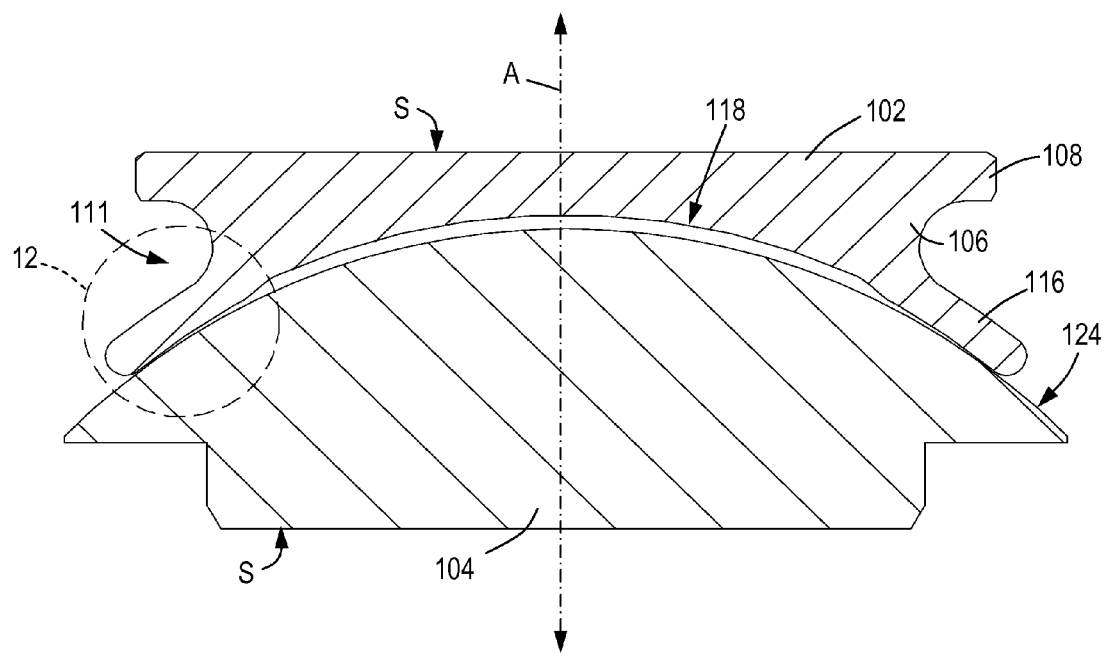
FIG. 10 is a cross-sectional view of the prosthetic joint of FIG. 9 in an unloaded condition.
Figure 11:
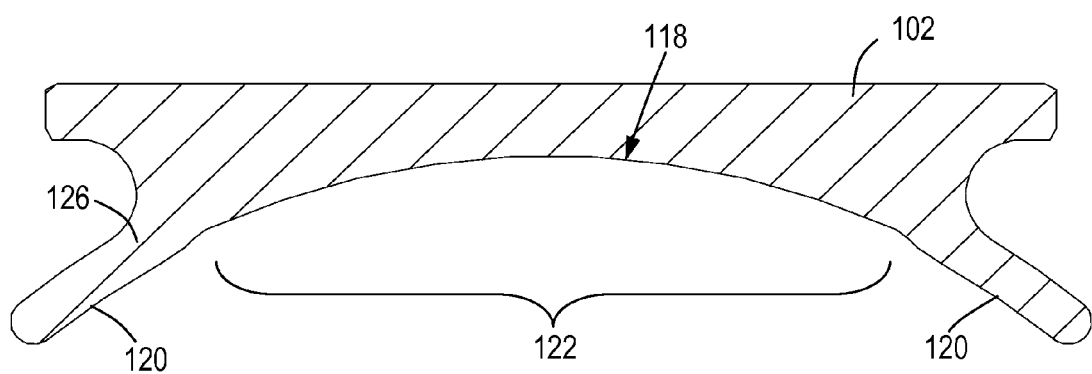
FIG. 11 is a cross-sectional view of one of the members of the prosthetic joint of FIG. 9.

FIGS. 9-14 illustrate a prosthetic joint 100 comprising first and second members 102 and 104. The illustrated prosthetic joint 100 is particularly adapted for a spinal application, but it will be understood that the principles described herein may be applied to any type of prosthetic joint. Both of the members 102 and 104 are bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 10, a central axis "A" passes through the centers of the first and second members 102 and 104 and is generally representative of the direction in which external loads are applied to the joint 100 in use. In the illustrated examples, the first and second joint members are bodies of revolution about this axis, but the principles of the present invention also extend to shapes that are not bodies of revolution.

The first member 102 includes a body 106 with a perimeter flange 116 extending in a generally radially outward direction at one end. Optionally, a disk-like base 108 may be disposed at the end of the body 106 opposite the flange 116, in which case a circumferential gap 111 will be defined between the base 106 and the flange 116. The first member 102 is constructed from a rigid material. As used here, the term "rigid" refers to a material which has a high stiffness or modulus of elasticity. Nonlimiting examples of rigid materials having appropriate stiffness for the purpose of the present invention include stainless steels, cobalt-chrome alloys, titanium, aluminum, and ceramics. By way of further example, materials such as polymers would generally not be considered "rigid" for the purposes of the present invention. Generally, a rigid material should have a modulus of elasticity of about $0.5 \times 10^6$ psi or greater. Collectively, one end of the body 106 and the flange 116 define a wear-resistant, concave first contact surface 118. As used herein, the term "wear-resistant" refers to a material which is resistant to surface material loss when placed under load. Generally the wear rate should be no more than about 0.5 μm (0.000020 in.) to about 1.0 μm (0.000040 in.) per million cycles when tested in accordance with ASTM Guide F2423. As a point of reference, it is noted that any of the natural joints in a human body can easily experience one million operating cycles per year. Nonlimiting examples of wear-resistant materials include solid metals and ceramics. Known coatings such as titanium nitride, chrome plating, carbon thin films, and/or diamond-like carbon coatings may be used to impart wear resistance to the first contact surface 118. Optionally, the first contact surface 118 could comprise a separate face layer (not shown) of a wear-resistant material such as ultra-high molecular weight (UHMW) polyurethane.

Figure 14:
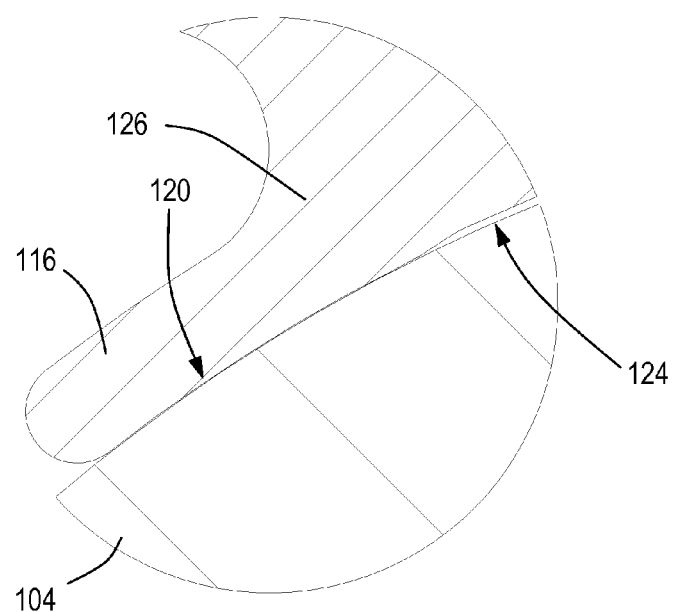
FIG. 14 is an enlarged view of a portion of FIG. 13.
Figure 15:
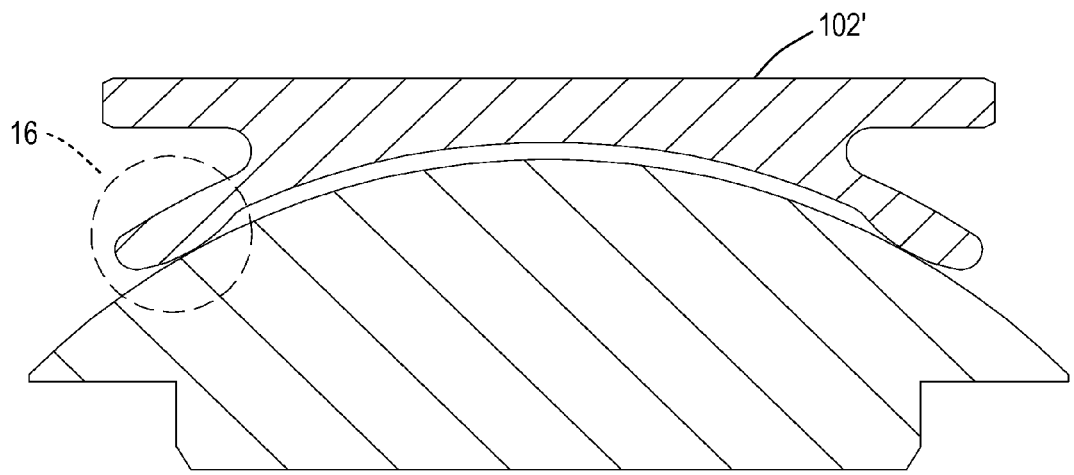
FIG. 15 is a cross-sectional view of an alternative joint member.
Figure 16:
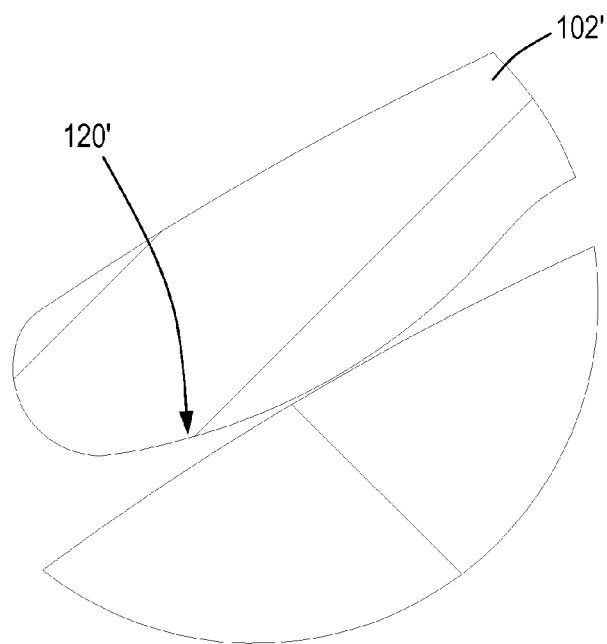
FIG. 16 is an enlarged view of a portion of FIG. 15.

The first contact surface 118 includes a protruding peripheral rim 120 (see FIG. 11), and a recessed central portion 122, which may also be considered a "pocket" or a "relief". As used herein, the term "recessed" as applied to the central portion 122 means that the central portion 122 lies outside of the nominal exterior surface of the second member 104 when the joint 100 is assembled. In one configuration, shown in FIGS. 9-14, and best seen in FIG. 11, the rim 120 is concave, with the radius of curvature being quite high, such that the cross-sectional shape of the surface of the rim 120 approaches a straight line. FIGS. 15 and 16 show another configuration of a joint member 102' in which the rim 120' has a convex-curved cross-sectional shape. The cross-sectional shape of the rim may be flat or curved as necessary to suit a particular application.

The annular configuration of first contact surface 118 with the protruding rim 120 results in a configuration which permits only pivoting and rotational motion, and is statically and dynamically determinate for the life of the joint 100. In contrast, prior art designs employing mating spherical shapes, even very accurate shapes, quickly reach a statically and dynamically indeterminate condition after use and wear. This condition accelerates wear, contributes to the fretting corrosion wear mechanism, and permits undesired lateral translation between the joint members.

The second member 104 is also made from a rigid material and has a wear-resistant, convex second contact surface 124. The first and second contact surfaces 118 and 124 bear directly against each other so as to transfer axial and lateral loads from one member to the other while allowing pivoting motion between the two members 102 and 104.

Nominally the first and second members 102 and 104 define a "ring" or "band" contact interface therebetween. In practice it is impossible to achieve surface profiles completely free of minor imperfections and variations. If the first and second members 102 and 104 were both completely rigid, this would cause high Hertzian contact stresses and rapid wear. Accordingly, an important feature of the illustrated joint 100 is that the flange 116 (and thus the first contact surface 118) of the first member 102 is conformable to the second contact surface 124 when the joint is placed under load.

Figure 12:
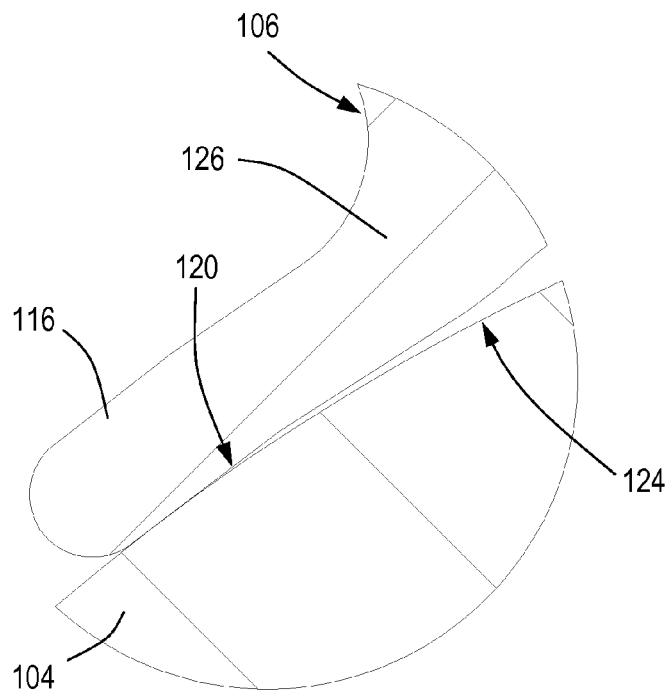
FIG. 12 is an enlarged view of a portion of FIG. 10.
Figure 13:
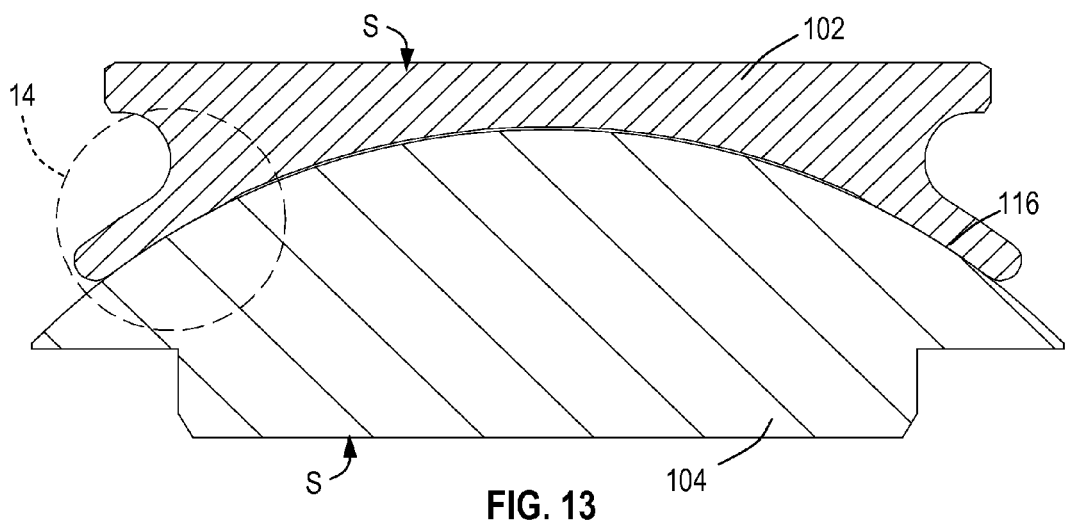
FIG. 13 is a cross-sectional view of the prosthetic joint of FIG. 9 in a loaded condition.

FIGS. 10 and 12 show a cross-sectional view of the flange 116 in an unloaded condition or free shape. It can be seen that the distal end of the rim 120 contacts the second contact surface 124, while the inboard end of the rim 120 (i.e. near where the flange 116 joins the body 106) does not. FIGS. 13 and 14 show the flange 116 in a deflected position or loaded shape, where substantially the entire section width of the rim 120 contacts the second contact surface 124, resulting in a substantially increased contact surface area between the two members 102 and 104, relative to the free shape. The rim 120' of the joint member 102' (see FIG. 16) is similarly conformable; however, given the curved cross-sectional shape, the total amount of surface contact area remains substantially constant in both loaded and unloaded conditions, with the rim 120' undergoing a "rolling" or "rocking" motion as the loading changes.

The conformable nature of the flange 116 is explained in more detail with reference to FIGS. 24 through 30. As noted above, the first member 102 has a flange 116 and a concave first contact surface 118. The second member 104 has a convex second contact surface 124. When assembled and in use the joint 100 is subject, among other loads, to axial loading in the direction of the arrows labeled "F" in FIG. 24 (i.e. along axis "A" of FIG. 10). As previously stated, it is impossible in practice for either of the contact surfaces 118 or 124 to be perfect surfaces (i.e. a perfect sphere or other curve or collection of curves). It is believed that in most cases that a defect such as a protrusion from the nominal contact surface of just 0.00127 mm (0.00005 in.), that is, 50 millionths of a inch, or larger, would be sufficient to cause fretting corrosion and failure of a metal-on-metal joint constructed to prior art standards. A defect may include a variance from a nominal surface shape as well as a discontinuity in the contact surface. Defects may arise through a variety of sources such as manufacturing, installation, and/or operating loads in the implanted joint.

Figure 25:
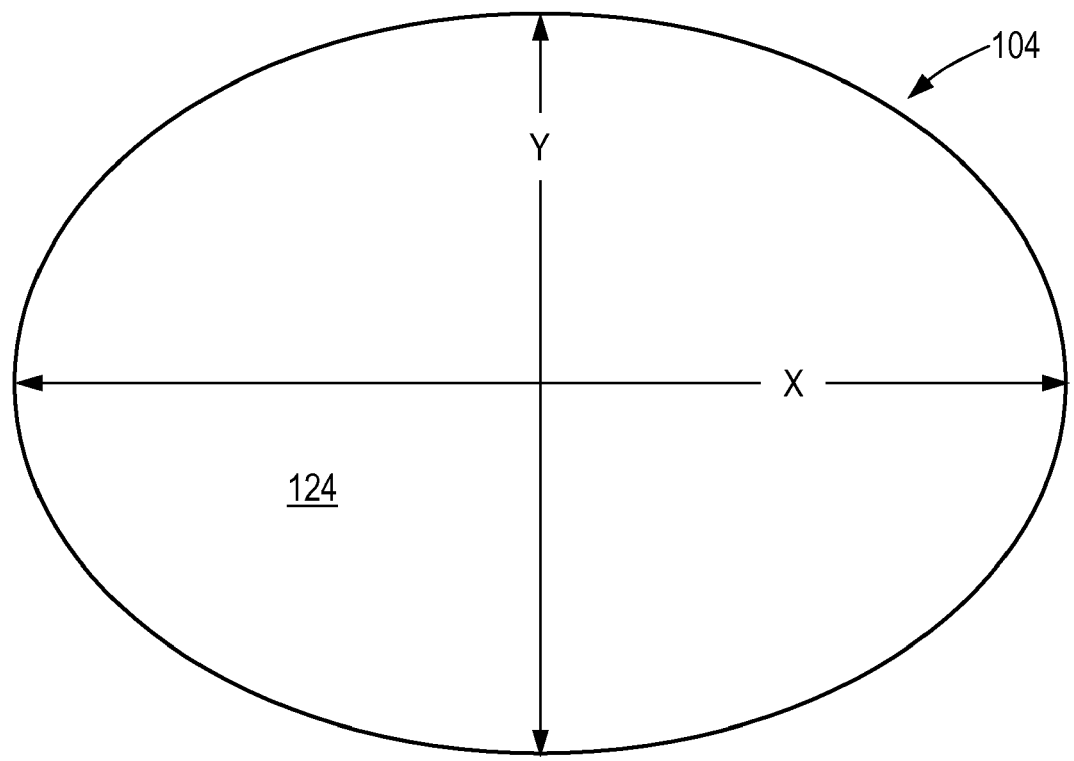
FIG. 25 is a top plan view of one of the joint members shown in FIG. 24.
Figure 26:
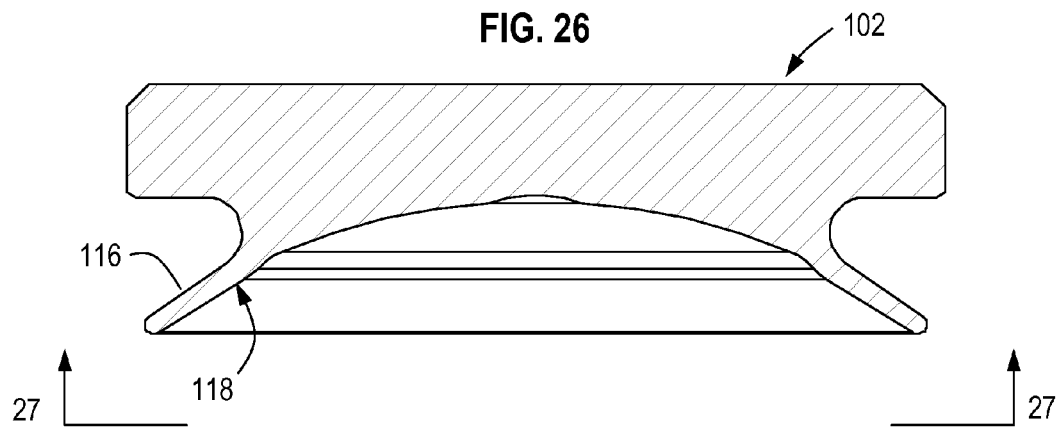
FIG. 26 is a cross-sectional view of one of the joint members shown in FIG. 24.
Figure 27:
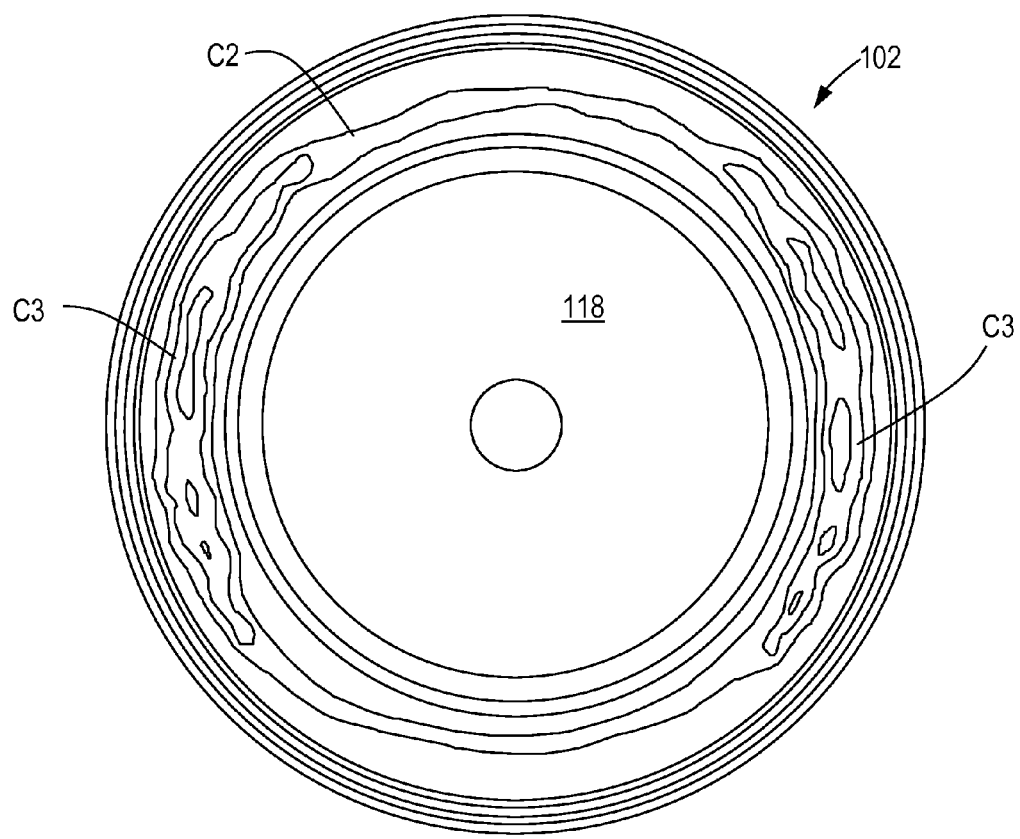
FIG. 27 is a contact stress plot of the joint member shown in FIG. 26.

FIG. 25 shows the second member 104 which in this particular example varies from a nominal shape in that it is elliptical rather than circular in plan view. The elliptical shape is grossly exaggerated for illustrative purposes. For reference, the dimensions of the second member 104 along the major axis labeled "X" is about 0.0064 mm (0.00025 in.) larger than its dimension along the minor axis labeled "Y". When assembled and loaded, the flange 116 conforms to the imperfect second contact surface 124 and deflects in an irregular shape. In other words, in addition to any uniform deflection which may be present, the deflected shape of the flange 116 includes one or more specific locations or portions that are deflected towards or away from the nominal free shape to a greater or lesser degree than the remainder of the flange 116. Most typically the deflected shape would be expected to be non-axisymmetric. For example, the deflection of the flange 116 at points located at approximately the three o'clock and nine o'clock positions is substantially greater than the deflection of the remainder of the flange 116. As a result, the contact stress in that portion of the first contact surface 118 is relieved. FIG. 27 is a plan view plot (the orientation of which is shown by arrow in FIG. 26) which graphically illustrates the expected contact stresses in the first contact surface 118 as determined by analytical methods. The first contour line "C2" shows that a very low level of contract stress is present around the entire perimeter of the first contact surface 118. This is because the entire first contact surface 118 is in contact with the second contact surface 124. Another contour line "C3" represents the areas of maximum contact stress corresponding to the protruding portions of the elliptical second contact surface 124.

Figure 28:
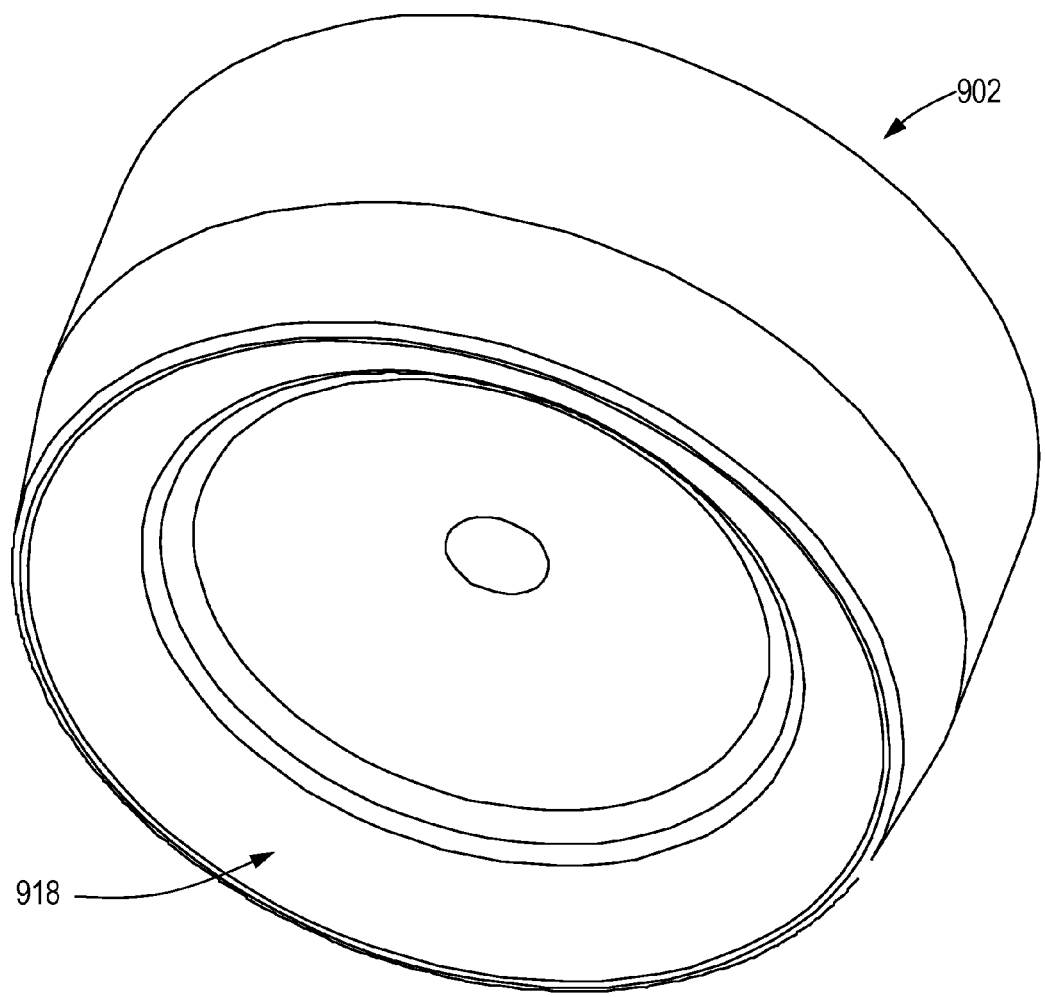
FIG. 28 is a perspective view of a rigid joint member used for comparison purposes.
Figure 29:
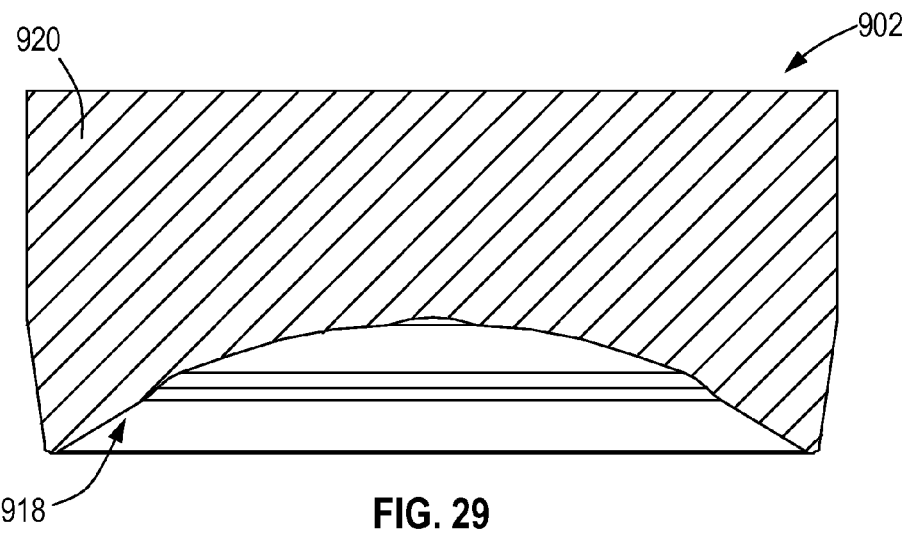
FIG. 29 is a cross-sectional view of the joint member shown in FIG. 28.
Figure 30:
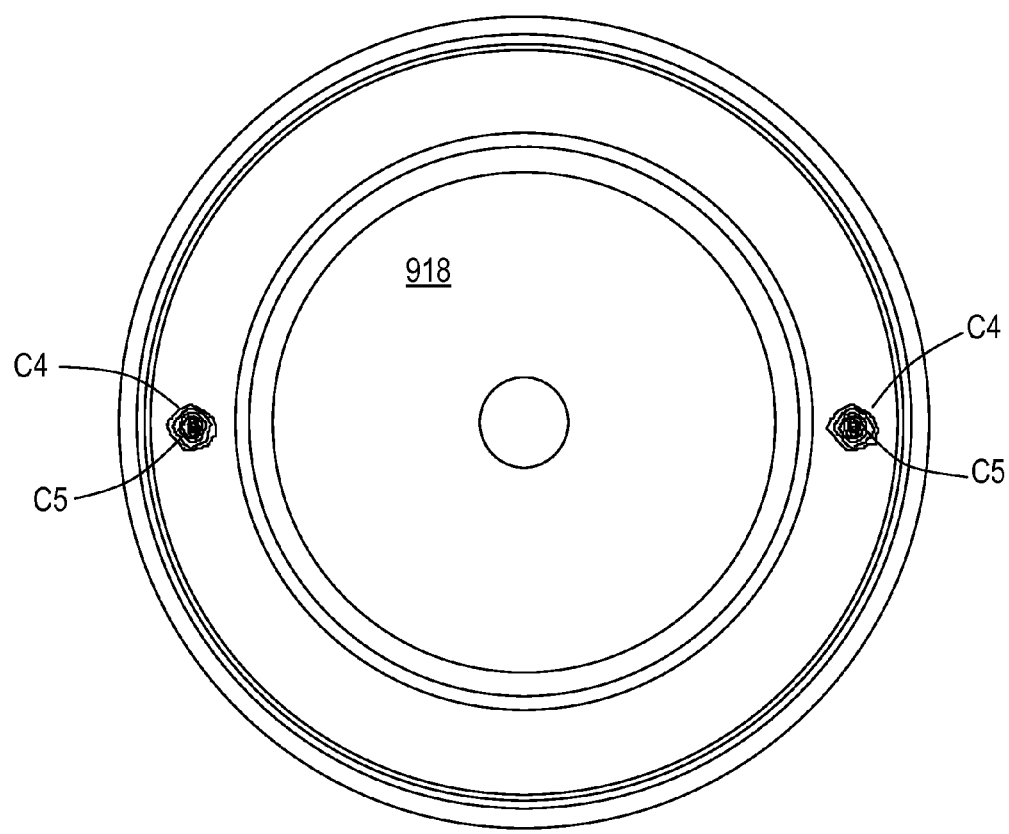
FIG. 30 is a contact stress plot of the joint member shown in FIG. 29.

For comparative purposes, FIGS. 28 and 29 depict a member 902 constructed according to prior art principles. The member 902 has a contact surface 918 with an identical profile and dimensions of the first contact surface 118 of the first member 102. However, consistent with the prior art, the member 902 has a massive body 920 behind the entire contact surface 918, rendering the entire member 902 substantially rigid. FIG. 30 graphically illustrates the expected contact stresses in the contact surface 918 as determined by analytical methods, when the member 902 is assembled and placed in contact with the second member 104, using the same applied load as depicted in FIG. 27. Because of the rigidity of the member 902, a "bridging" effect is present wherein contact between the contact surfaces (one of which is circular in plan view, and the other of which is elliptical) effectively occurs at only two points, located at approximately the three o'clock and nine o'clock positions. A first contour line "C4" shows two discrete areas where the lowest level of contract stress is present. These lines are not contiguous because there is no contact in the remaining area of the contact surfaces (for example at the six o'clock and twelve o'clock positions). Another contour line "C5" represents the areas of maximum contact stress. Analysis shows a peak contact stress having a magnitude of two to twenty times (or more) the peak contact stress of the inventive joint as shown in FIG. 27.

To achieve this controlled deflection, the flange 116 is thin enough to permit bending under working loads, but not so thin as to allow material yield or fatigue cracking. The deflection is opposed by the elasticity of the flange 116 in bending, as well as the hoop stresses in the flange 116. To achieve long life, the first member 102 is sized so that stresses in the flange 116 will be less than the endurance limit of the material, when a selected external load is applied. In this particular example, the joint 100 is intended for use between two spinal vertebrae, and the design average axial working load is in the range of about 0 N (0 lbs) to about 1300 N (300 lbs.). These design working loads are derived from FDA-referenced ASTM and ISO standards for spinal disc prostheses. In this example, the thickness of the flange 116, at a root 126 where it joins the body 106 (see FIG. 12) is about 0.04 mm (0.015 in.) to about 5.1 mm (0.200 in.), where the outside diameter of the flange 116 is about 6.4 mm (0.25 in.) to about 7.6 cm (3.0 in.).

Figure 17:
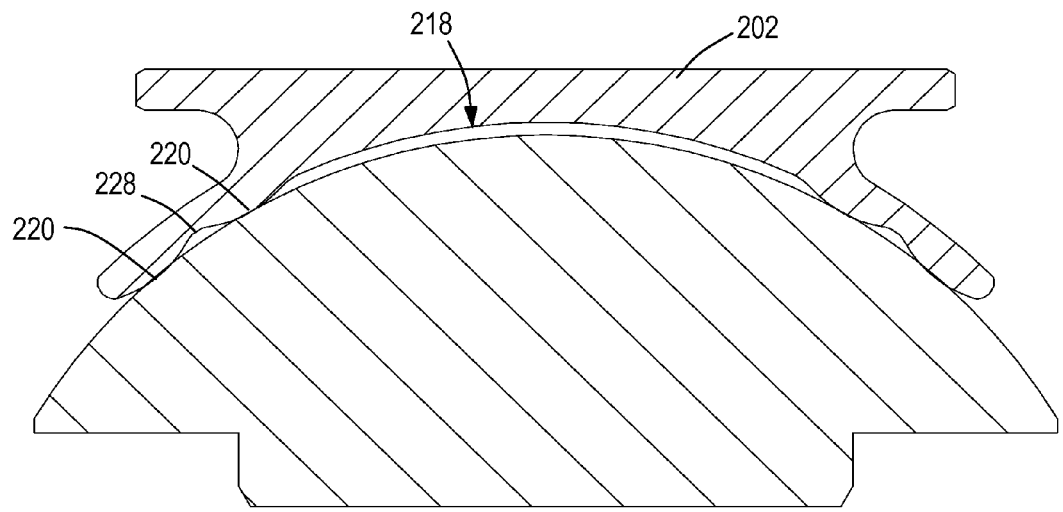
FIG. 17 is a cross-sectional view of another alternative joint member.

The joint members may include multiple rims. For example, FIG. 17 illustrates a joint member 202 where the first contact surface 218 includes two protruding rims 220, with a circumferential groove or relief area 228 therebetween. The presence of multiple rims increases the contact surface areas between the two joint members.

Figure 18:
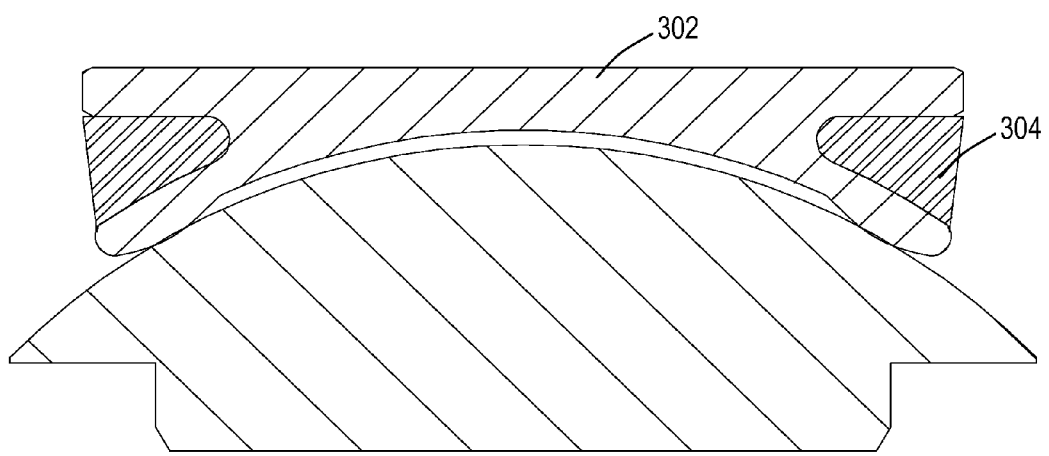
FIG. 18 is a cross-sectional view of another alternative joint member including a filler material.

If present, the circumferential gap between the flange and the base of the joint member may be filled with resilient nonmetallic material to provide damping and/or additional spring restoring force to the flange. FIG. 18 illustrates a joint member 302 with a filler 304 of this type. Examples of suitable resilient materials include polymers, natural or synthetic rubbers, and the like.

Figure 19:
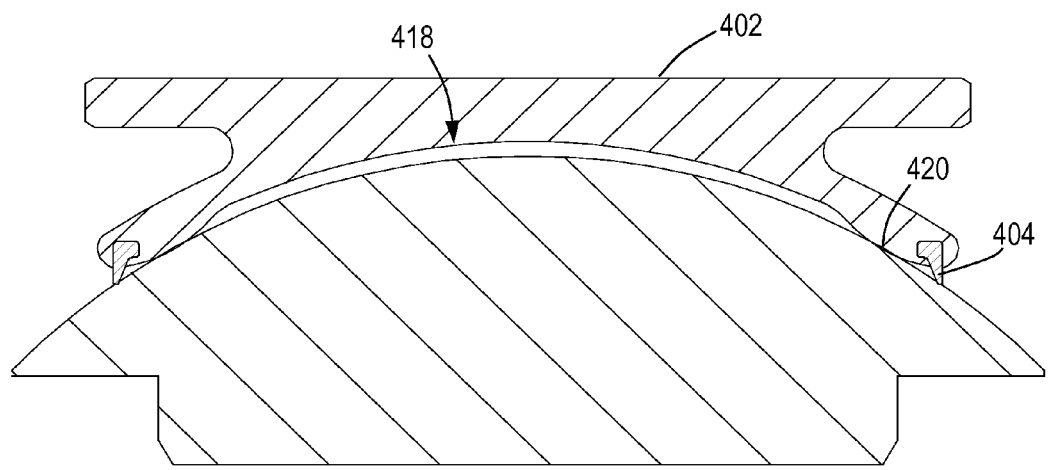
FIG. 19 is a cross-sectional view of another alternative joint member including a wiper seal.

As discussed above, the joint may incorporate a wiper seal. For example, FIG. 19 illustrates a joint member 402 with a resilient wiper seal 404 protruding from the rim 420 of the first contact surface 418. The wiper seal 404 keeps particles out of the contact area (seal void), while containing working fluid (natural or synthetic). The seal geometry is intended to be representative and a variety of seal characteristics may be employed; such as a single lip seal, a double or multiple lip seal. A pad or wiper seal may be made from a variety of material options. Different seal mounting options may be used, for example a lobe in shaped groove as shown in FIG. 18, a retaining ring or clamp, adhesion substance. The seal may also be incorporated into the contact face of the interface zone.

Figure 20:
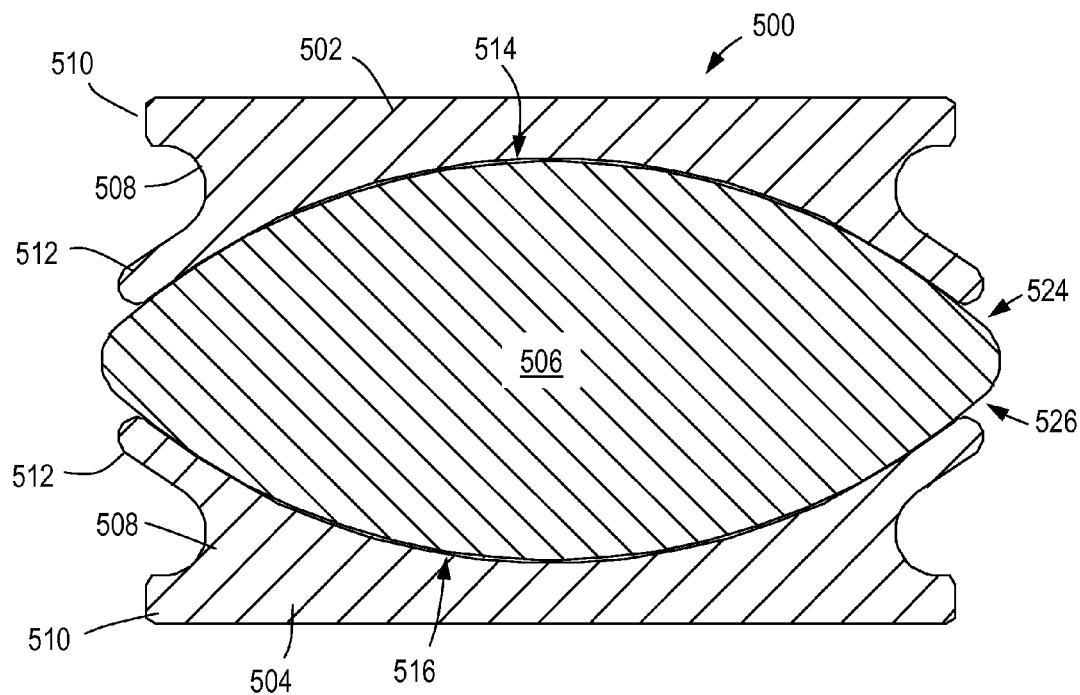
FIG. 20 is a cross-sectional view of another alternative prosthetic joint.

The joint construction described above can be extended into a three-part configuration. For example, FIG. 20 illustrates a prosthetic joint 500 having first, second, and third members 502, 504, and 506. The first and second members 502 and 504 are similar in construction to the first member 102 described above, and each includes a body 508, an optional disk-like base 510, and a flange 512. The flanges 512 define wear-resistant concave first and second contact surfaces 514 and 516, each of which includes a protruding peripheral rim, and a recessed central portion as described above. The third member 506 has a double-convex shape defining opposed wear-resistant, convex third and fourth contact surfaces 524 and 526. The first and second 514 and 516 bear against the third and fourth contact surfaces 524 and 526, respectively, so as to transfer axial (i.e. compression) and lateral loads between the first and second members 502 and 504 through the third member 506, while allowing pivoting motion between the members 502, 504, and 506. The first and second contact surfaces 514 and 516 are conformal to the third and fourth contact surfaces 524 and 526 as described in more detail above.

Figure 21:
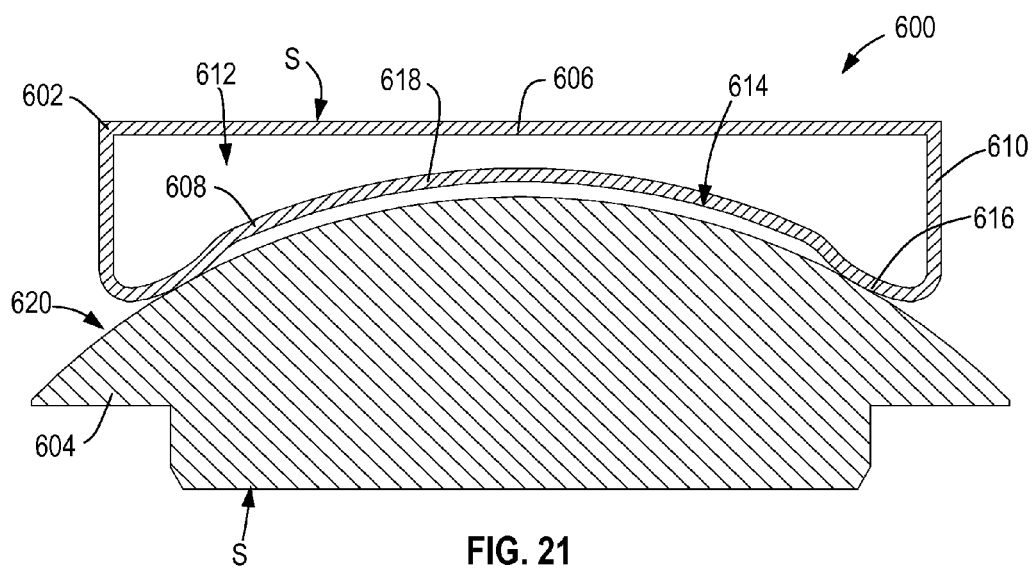
FIG. 21 is a cross-sectional view of a prosthetic joint constructed in accordance with another aspect of the present invention.

FIG. 21 illustrates an alternative prosthetic joint 600 comprising first and second members 602 and 604 constructed from rigid materials. Both of the members 602 and 604 are bone-implantable, meaning they include osseointegration surfaces, labeled "S", as described in more detail above.

The first member 602 is hollow and includes a disk-like base 606 and a cup 608, interconnected by a peripheral wall 610. An interior cavity 612 is defined between the base 606 and the cup 608. The cup 608 is constructed from a rigid material and defines a wear-resistant, concave first contact surface 614. The first contact surface 614 includes a protruding peripheral rim 616, and a recessed central portion 618, which may also be considered a "pocket" or a "relief". The rim 616 may have a conical or curved cross-sectional shape.

The second member 604 is constructed from a rigid material and has a wear-resistant, convex second contact surface 620. The first and second contact surfaces 614 and 616 bear directly against each other so as to transfer axial and laterals loads from one member to the other while allowing pivoting motion between the two members 602 and 604.

As described above with reference to the prosthetic joint 100, the cup 606 of the first member 602 is thin enough to permit bending under working loads, but not so thin as to allow material yield or fatigue cracking. The first contact surface 614 is thus conformable to the second contact surface 620 when the prosthetic joint 600 is placed under external load.

Figure 22:
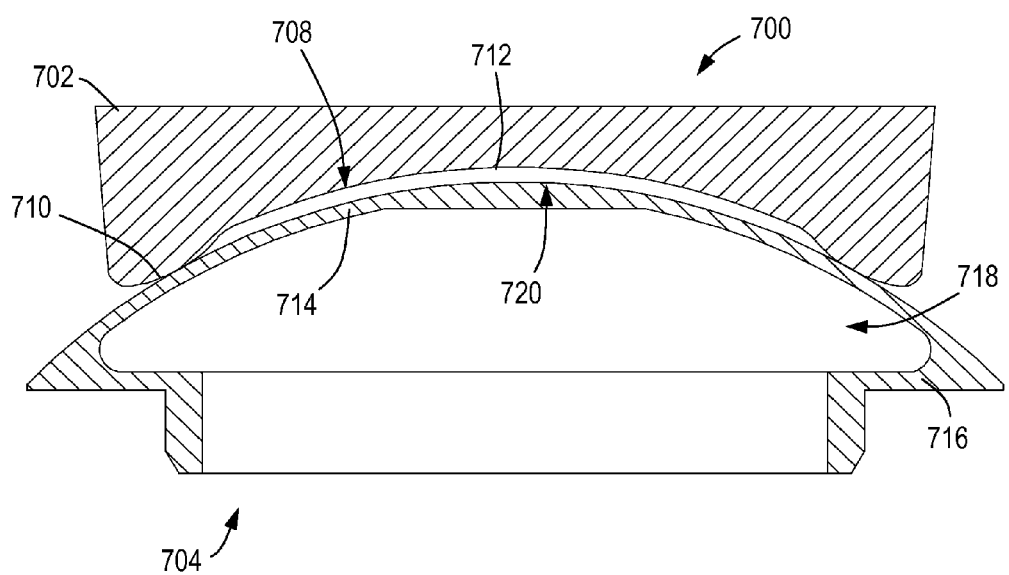
FIG. 22 is a cross-sectional view of a prosthetic joint constructed in accordance with yet another aspect of the present invention.

An inverted configuration of hollow members is also possible. For example, FIG. 22 illustrates a prosthetic joint 700 comprising first and second members 702 and 704, both constructed of rigid materials. The first member 702 is solid and includes a wear-resistant, concave first contact surface 708. The first contact surface 708 includes a protruding peripheral rim 710, and a recessed central portion 712, which may also be considered a "pocket" or a "relief".

The second member 704 is hollow and includes a dome 714 connected to a peripheral wall 716. An interior cavity 718 is defined behind the dome 714. The dome 714 defines a wear-resistant, convex second contact surface 720, which is shaped and sized enough to permit bending under working loads, but not so as to allow material yield or fatigue cracking The second contact surface 720 is thus conformable to the first contact surface 708 when the prosthetic joint 700 is placed under external load.

Figure 23:
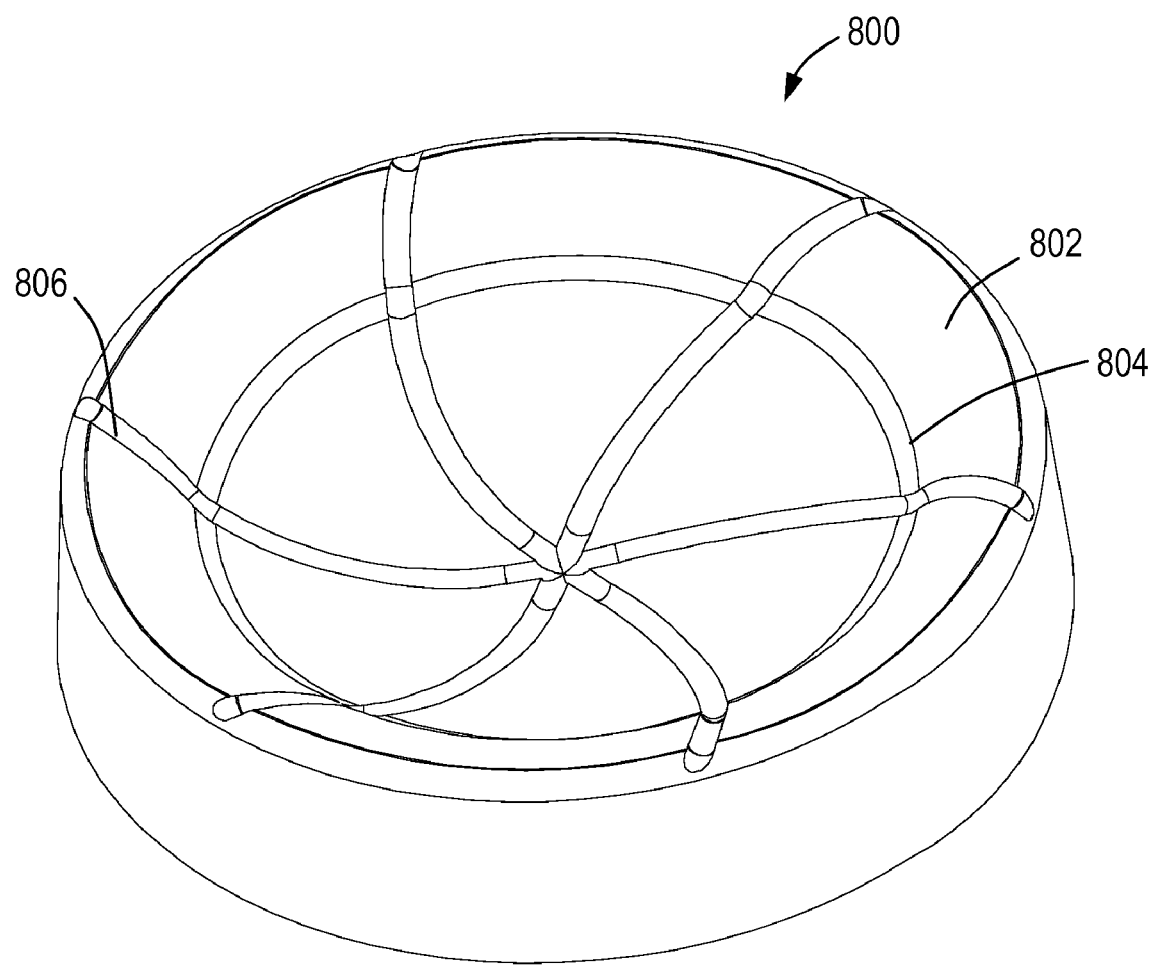
FIG. 23 is a perspective view of a joint member having a grooved surface.
Figure 24:
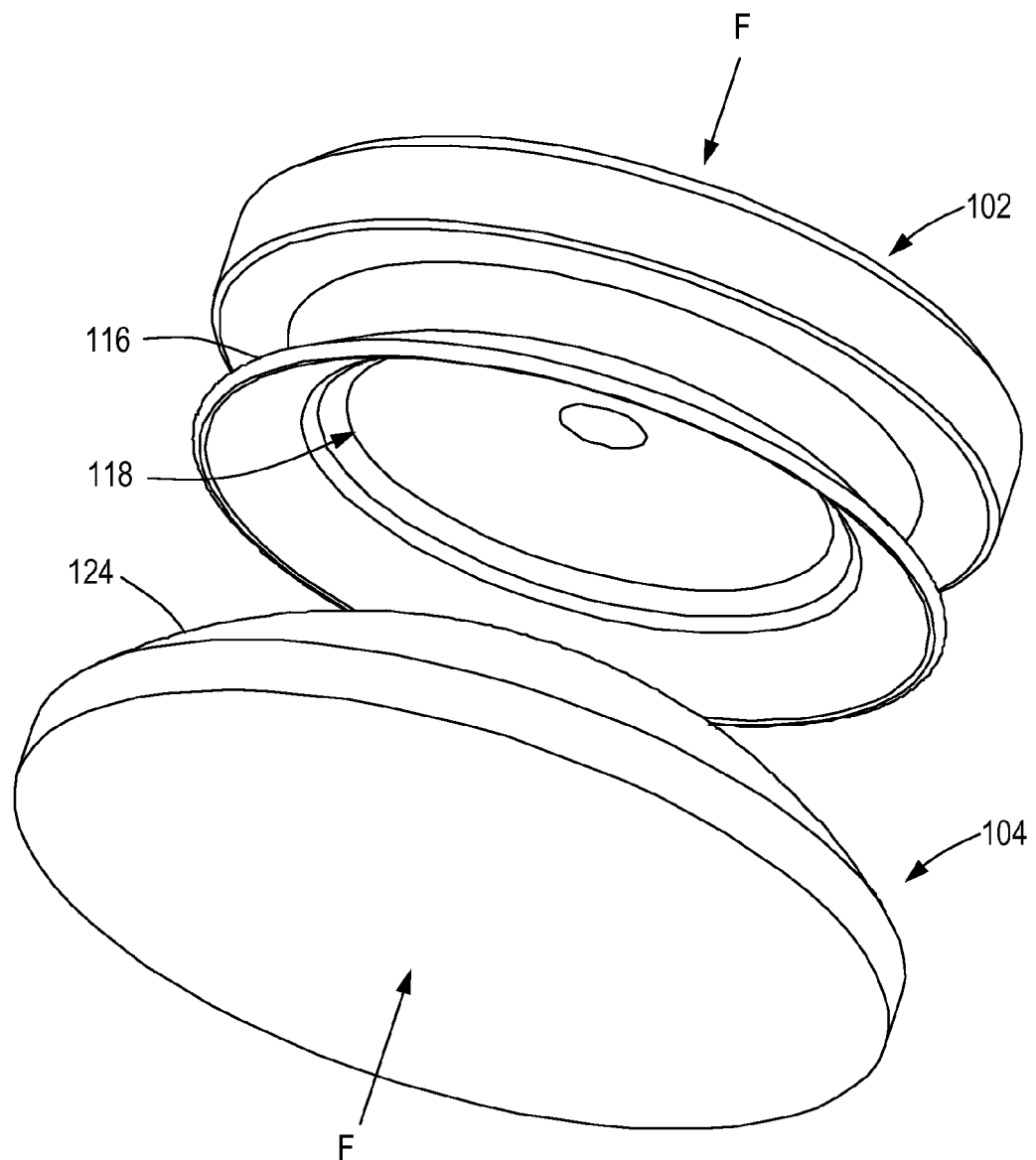
FIG. 24 is a exploded perspective view of two mating joint members.

The first and second contact surfaces 708 and 720 bear directly against each other so as to transfer axial and lateral loads from one member to the other while allowing pivoting motion between the two members 702 and 704. Any of the contact surfaces described above may be provided with one or more grooves formed therein to facilitate flow of fluid or debris. For example, FIG. 23 illustrates a joint member 800 including a concave contact surface 802. The contact surface 802 includes a circular groove 804, and plurality of generally radially-extending grooves 806 which terminate at the center of the contact surface 802 and intersect the circular groove 804.

Figure 31:
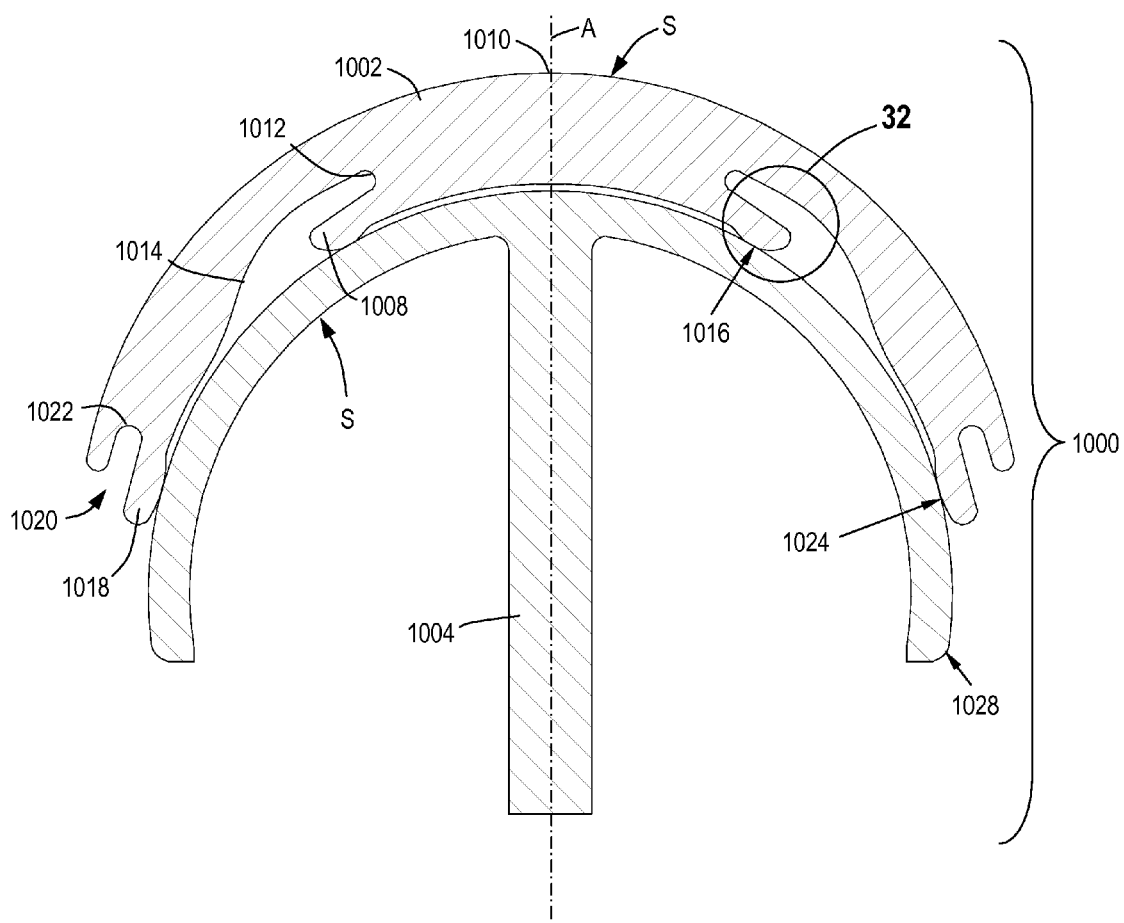
FIG. 31 is a cross-sectional view of a prosthetic joint constructed in accordance with another aspect of the present invention.
Figure 32:
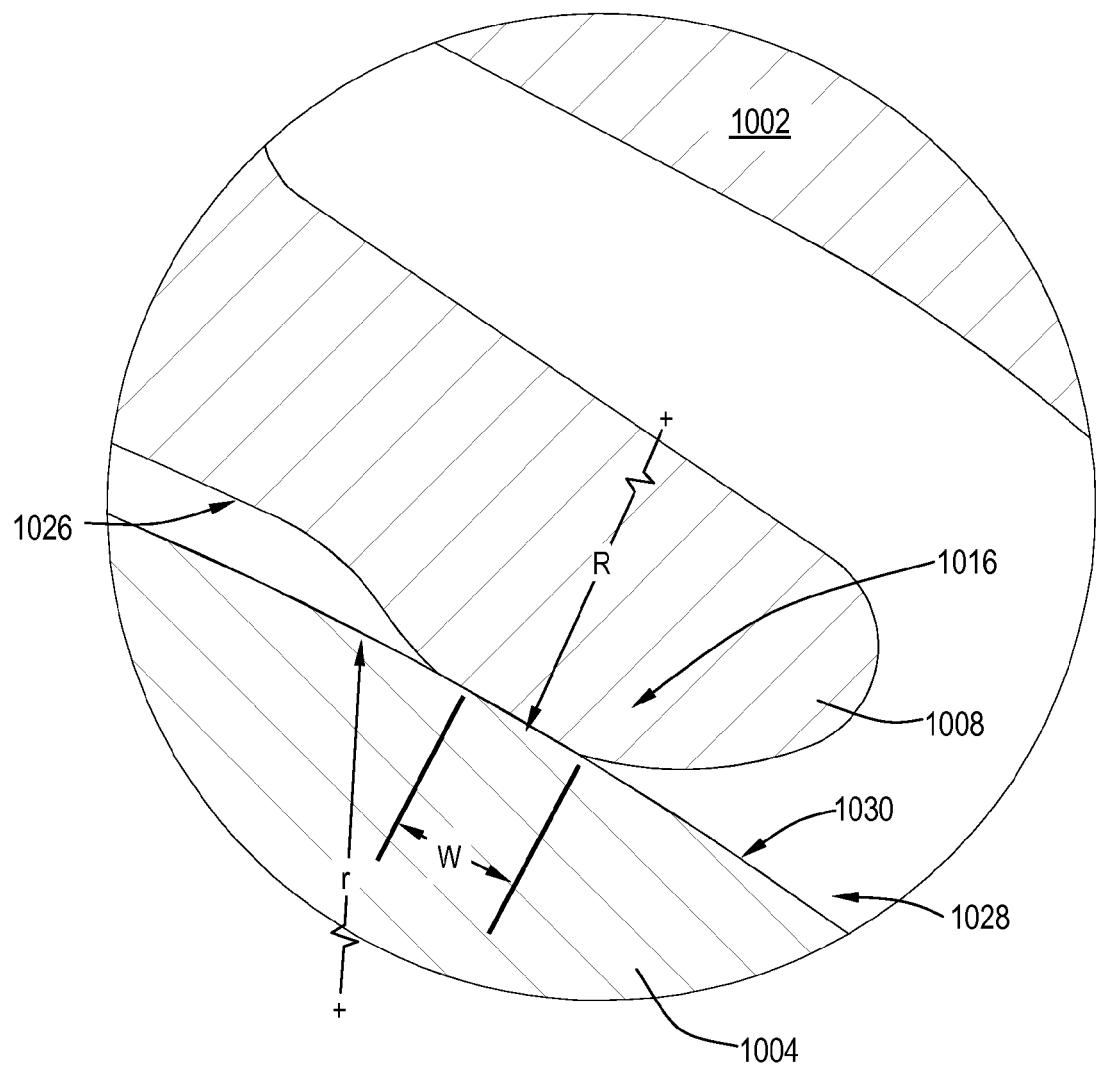
FIG. 32 is an enlarged view of a portion of the joint shown in FIG. 31.
Figure 33:
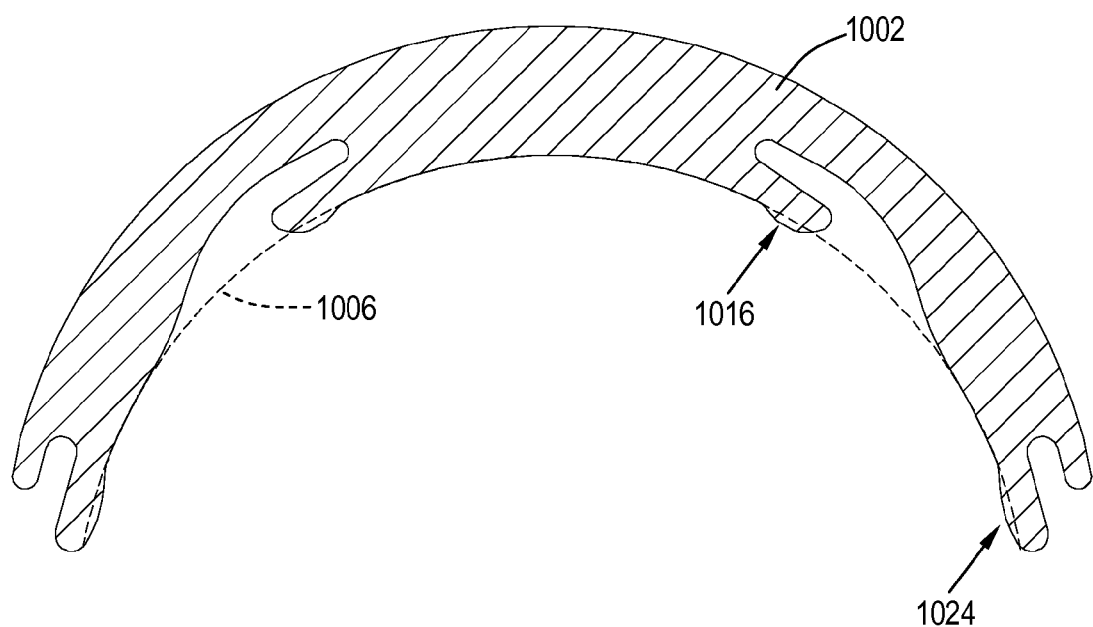
FIG. 33 is a cross-sectional view of a cup member of the joint shown in FIG. 31.

FIGS. 31-33 illustrate an alternative prosthetic joint 1000 comprising first and second members 1002 and 1004. The illustrated prosthetic joint 1000 is particularly adapted for a ball-and-socket joint application such as is found in a human hip joint (i.e. the acetabulofemoral joint) or shoulder joint (i.e. the glenohumeral joint), but it will be understood that the principles described herein may be applied to any type of prosthetic joint. Both of the members 1002 and 1004 are bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 31, a nominal central axis "A" passes through the centers of the first and second members 1002 and 1004 In the illustrated examples, the first and second joint members 1002 and 1004 are bodies of revolution about this axis, but the principles of the present invention also extend to non-axisymmetric shapes.

The first member 1002 is constructed from a rigid material as described above. The first member 1002 is concave and may generally be thought of as a "cup", although it need not have any particular degree of curvature. Its interior defines a nominal cup surface 1006 shown by the dashed line in FIG. 33. The interior includes an annular first flange 1008 which is located relatively near an apex 1010 of the first member 1002 and which extends in a generally radial direction relative to the axis A. The first flange 1008 is defined in part by an undercut groove 1012 formed in the first member 1002. A ramped surface 1014 forms a transition from the groove 1012 to the nominal cup surface 1006. The first flange 1008 includes a protruding first contact rim 1016. As used herein, the term "protruding" as applied to the first contact rim 1016 means that the first contact rim 1016 lies inside of the nominal cup surface 1006 when the joint 1000 is assembled. The first contact rim 1016 may have a curved or toroidal cross-sectional shape.

The interior also includes an annular second flange 1018 which is located at or near an outer peripheral edge 1020 of the first member 1002 and which extends in a generally axial direction relative to the axis A. The second flange 1018 is defined in part by an undercut groove 1022 formed in the first member 1002. The second flange 1018 includes a protruding second contact rim 1024. As used herein, the term "protruding" as applied to the second contact rim 1024 means that the second contact rim 1024 lies inside of the nominal cup surface 1006 when the joint 1000 is assembled. The second contact rim 1024 may have a curved or toroidal cross-sectional shape. Depending on the particular application, joint 1000 may include more than two flanges defining more than two contact rims.

In the illustrated example, the first member 1002 includes a face layer 1026 of a known coating such as titanium nitride, chrome plating, carbon thin films, and/or diamond-like carbon coatings, and/or a another wear-resistant material such as ultra-high molecular weight (UHMW) polyurethane. This face layer 1026 is used to impart wear resistance, as described above. The face layer 1026 may be extraordinarily thin. In this particular example, its as-applied thickness is about 0.0041 mm (0.00016 in.), or 160 millionths of a inch thick. The face layer 1026 is applied at a substantially uniform thickness over the surface profile which is defined by machined or formed features of the substrate. Alternatively, and especially if a much thicker face layer were used, the face layer could be profiled so as to define both the nominal cup surface 1006 and the first and second contact rims 1016 and 1024.

The second member 1004 is also made from a rigid material and has a wear-resistant, convex contact surface 1028. In the specific example illustrated, the second member 1004 includes a face layer 1030 of a known coating such as titanium nitride, chrome plating, carbon thin films, and/or diamond-like carbon coatings, and/or a another wear-resistant material such as ultra-high molecular weight (UHMW) polyurethane. This face layer 1030 is used to impart wear resistance, and may be quite thin, as described above. The first and second contact rims 1016 and 1024 bear directly against the contact surface 1028 so as to transfer axial and lateral loads from one member to the other while allowing pivoting motion between the two members 1002 and 1004.

The annular configuration of contact rims 1016 and 1024 results in a joint configuration which permits only pivoting and rotational motion, and is statically and dynamically determinate for the life of the joint 1000. In particular, the presence of the relatively widely-spaced contact rims 1016 and 1024, and the peripheral positioning of the second contact rim 1024 is highly effective in resisting any translation of the first and second members 1002 and 1004 lateral to the axis A.

Nominally the first and second contact rims 1016 and 1024 define two separate "ring" or "band" contact interfaces with the contact surface 1028 of the second member 1004. In practice it is impossible to achieve surface profiles completely free of minor imperfections and variations. If the first and second members 1002 and 1004 were both completely rigid, this would cause high Hertzian contact stresses (i.e. non-uniform contact) and rapid wear. Accordingly, an important feature of the illustrated joint 1000 is that the flanges 1008 and 1018 (and thus the contact rims 1016 and 1024) of the first member 1002 are conformable to the contact surface 1028 when the joint 1000 is placed under load. The flanges 1008 and 1018 can conform to the imperfect contact surface 1028 and deflect in an irregular shape. In other words, in addition to any uniform deflection which may be present, the deflected shape of the flanges 1008 and 1018 can include one or more specific locations or portions that are deflected towards or away from the nominal free shape to a greater or lesser degree than the remainder of the flanges 1008 and 1018. To achieve this controlled deflection, the flanges 1008 and 1018 are thin enough to permit bending under working loads, but not so thin as to allow material yield or fatigue cracking, or to exceed the endurance limit of the material. The deflection is opposed by the elasticity of the flanges 1008 and 1018 in bending, as well as the hoop stresses in the flanges 1008 and 1018.

Figure 36:
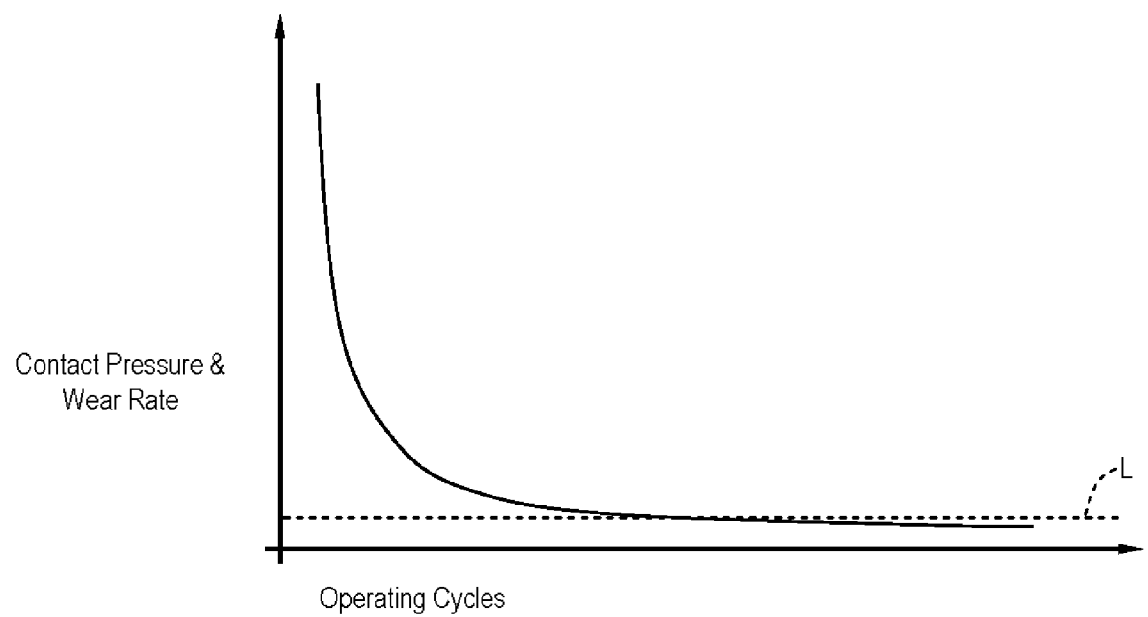
FIG. 36 is a graph showing contact pressure of the joint of FIG. 31 compared to the number of operating cycles.

The contact rims 1016 and 1024 are designed in conjunction with the contact surface 1028 to create a wear characteristic that is constantly diminishing (similar to an asymptotic characteristic). With reference to FIG. 32, the as-manufactured or initial curvatures (e.g. radii) of the first and second contact rims 1016 and 1024, denoted "R" are different from the curvature (e.g. radius) of the contact surface 1028, denoted "r". It is noted that the direction of curvature (i.e. the convexity or second derivative shape) of the first and second contact rims 1016 and 1024 may be the same as, or opposite to, that of the contact surface 1028 upon initial manufacture. In this example they are opposite. When assembled and placed under load, the annular interface between each of the contact rims 1016 and 1024 and the contact surface 1028 will have a characteristic width denoted "W", (effectively creating a contact band). The initial dimensions R and r are selected such that, even using highly wear-resistant surfaces or coatings, some wear takes place during an initial wear-in period of movement cycles. As a result, the contact band width W increases during the initial wear-in period. This increases contact area and therefore decreases contact stress for a given load. After the initial wear-in period (which preferably occurs before the joint is implanted), the contact band reaches a post wear-in width at which the contact stress is below a selected limit, below which the rate of wear in the contacting surfaces approaches a very low number or zero, consistent with a long life of the joint 1000. FIG. 36 illustrates this wear characteristic, with the limit "L" depicted as a horizontal line.

Figure 34:
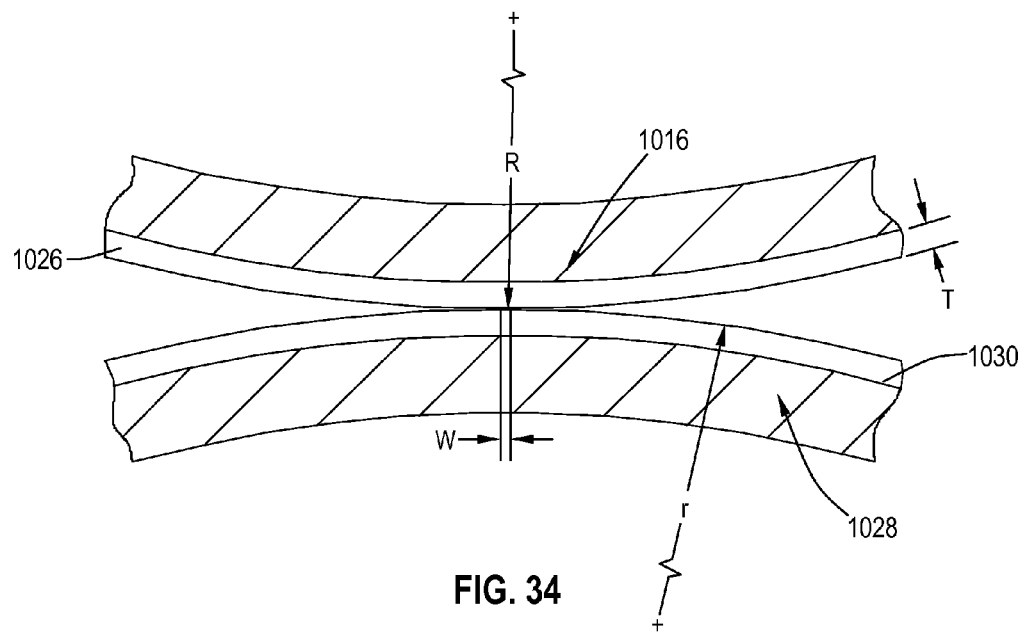
FIG. 34 is a greatly enlarged cross-sectional view of a portion of the joint shown in FIG. 31 in an initial condition.
Figure 35:
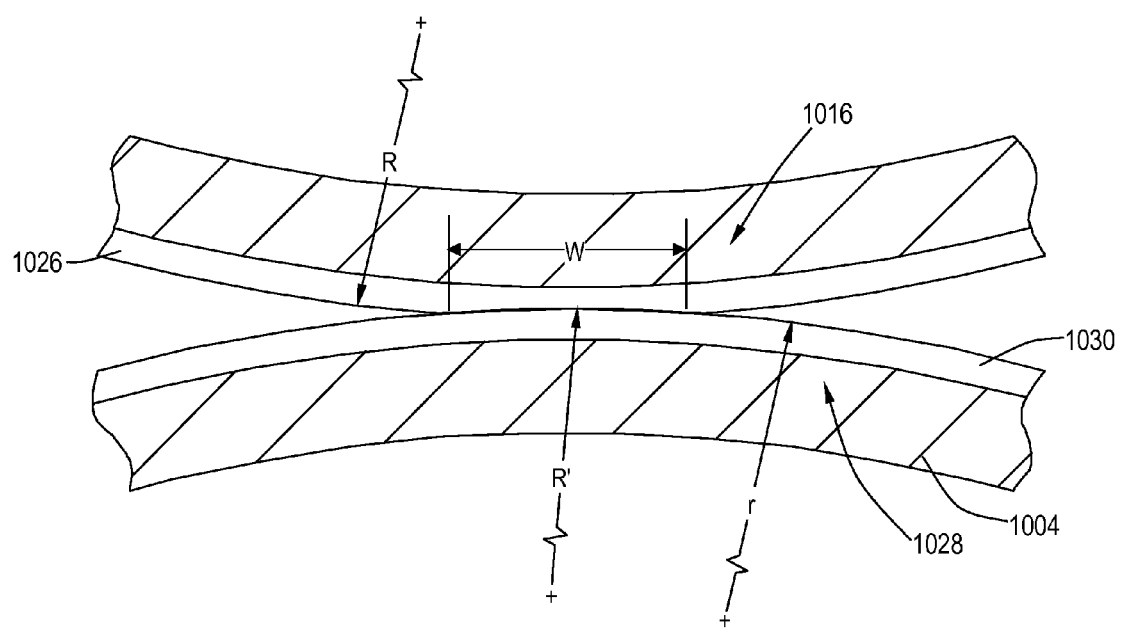
FIG. 35 is a greatly enlarged cross-sectional view of a portion of the joint shown in FIG. 31 after an initial wear-in period.

FIGS. 34 and 35 are schematic views showing the initial wear-in of the surface of the contact rim 1016 at a microscopic (or nearly microscopic) level. It will be understood that these figures are greatly exaggerated for the purposes of illustration. On initial manufacture, as shown in FIG. 34, the curvatures R and r of the contact rim 1016 and the contact surface 1028 have opposite directions. When assembled, the contact band width W is some nominal value, for example about 0.03 mm (0.001 in.), and the total thickness "T" of the face layer 1026 is at its as-applied value of about 0.0041 mm (0.00016 in.) for example. The action of the wear-in period described causes the face layer 1026 to wear to a shape complementary to the contact surface 1028. After this wear-in period the curvature of the portion of the contact rim 1016 within the contact band, denoted "R'", and the curvature r of the contact surface 1028 are in the same direction, and the values of the two curvatures are substantially the same. For example, the thickness T at the location of the contact band may decrease by about 0.0004 mm (0.000014 in.), with a corresponding increase in the width of the contact band W to about 0.2 mm (0.008 in.). Analysis shows that this increase in contact band width and surface area can reduce mean contact pressure by over 80%.

The configuration of the flanges 1008 and 1018 are important in developing the constantly diminishing wear characteristics described above. In particular, the flanges 1008 and 1018 are sized and shaped so that deflections of the contact rims 1016 and 1024 under varying load are always essentially normal to their respective tangent points on the opposing contact surface 1028, as the joint 1000 is loaded and unloaded. This ensures that the position of each of the contact bands remains constant and that the contact bands remain substantially uniform around the entire periphery of the joint 1000.

Figure 37:
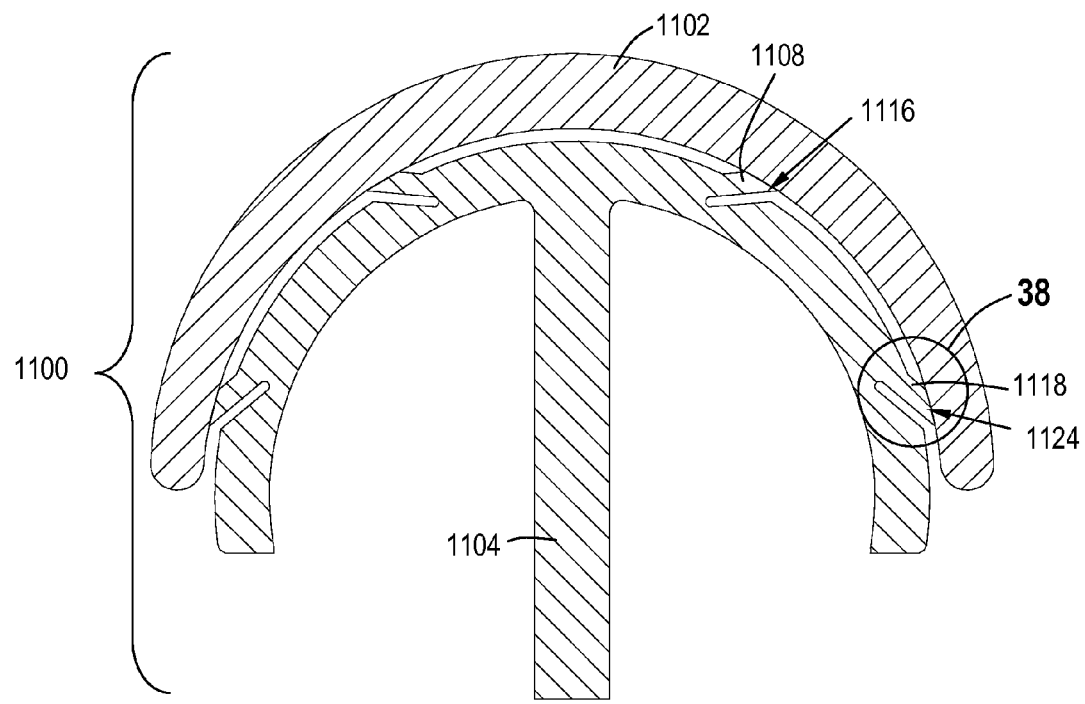
FIG. 37 is a cross-sectional view of a prosthetic joint constructed in accordance with another aspect of the present invention.
Figure 38:
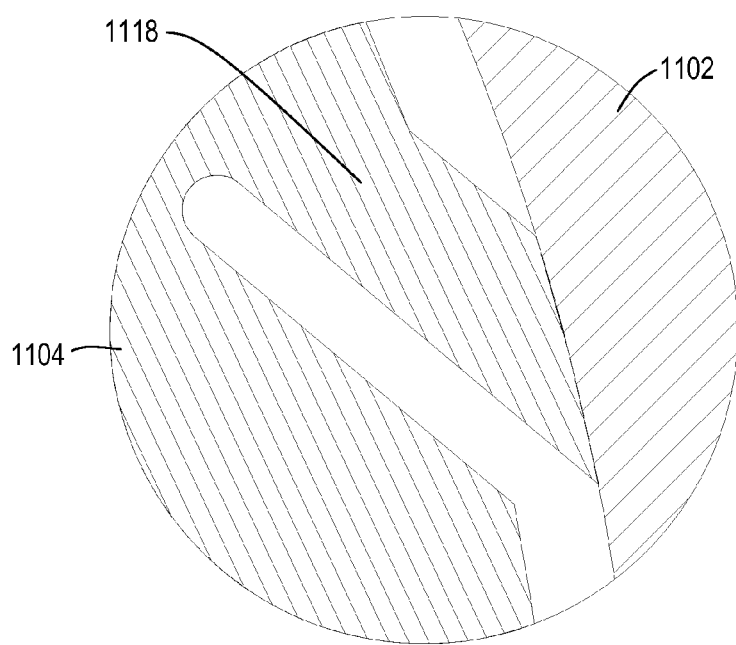
FIG. 38 is an enlarged view of a portion of the joint shown in FIG. 37.

An inverted configuration of the joint described above may be used. For example, FIGS. 37 and 38 illustrate a prosthetic joint 1100 having first and second members 1102 and 1104 which are substantially similar in general construction to the members of the joint 1000 described above in terms of materials, coatings, and so for forth. However, in this joint 1100, the concave member 1102 has a contact surface without protruding rings. The convex member 1104 has first and second flanges 1108 and 1118 which define first and second contact rims 1116 and 1124 which function in the same manner that the flanges and contact rims described above.

FIGS. 39-44 illustrate a prosthetic knee joint 2000. While the illustrated prosthetic joint 2000 is particularly adapted to replace the natural joint application such found in a human knee, it will be understood that the principles described herein may be applied to any type of prosthetic joint which requires similar movements. The main components of the joint 2000 are a femoral member 2002 and a tibial assembly 2004.

The femoral member 2002 is constructed from a rigid material as described above. The femoral member 2002 is generally "U"-shaped in side elevation. One leg of the "U" shape is divided by a slot 2006 into two separate, parallel fingers 2008. The femoral member 2002 includes an inner surface 2010 which is shaped for convenient and secure attachment to the lower end of a patient's femur (not shown). In this particular example the inner surface 2010 comprises a series of planar surfaces or facets. The inner surface 2010 may be configured as an osseointegration surface, i.e., a surface designed to be infiltrated by bone growth to improve the connection between the implant and the bone. Osseointegration surfaces may be made from materials such as TRABECULAR METAL, textured metal, or sintered or extruded implant integration textures, as described above. The femoral member 2002 may be mounted to a patient's femur using a press fit in a known manner, or partially or fully cemented to the femur in a known manner. The outer surface of the femoral member 2002 is a femoral contact surface 2012. Its surface profile includes two protruding ridges 2014 (see FIG. 41) each having a convex cross-sectional shape. Each ridge 2014 runs along one of the fingers 2008 and extends around the "U" shape. These ridges 2014 correspond to the lateral and medial condyles of a human femur and may be interchangeably referred to herein as "condyles". The curvature of the "U" shape in side elevation view (and thus the curvature of the ridges 2014 along their arc length), indicated schematically at "C" in FIG. 40, may be a constant or variable radius.

The femoral contact surface 2012 is wear-resistant, as that term is defined above. In the specific example illustrated, the femoral contact surface 2012 includes a face layer (not depicted separately) of a known coating such as titanium nitride, chrome plating, carbon thin films, and/or diamond-like carbon coatings, and/or a another wear-resistant material such as ultra-high molecular weight (UHMW) polyurethane. This face layer is used to impart wear resistance, and may be quite thin, as described above.

Figure 42:
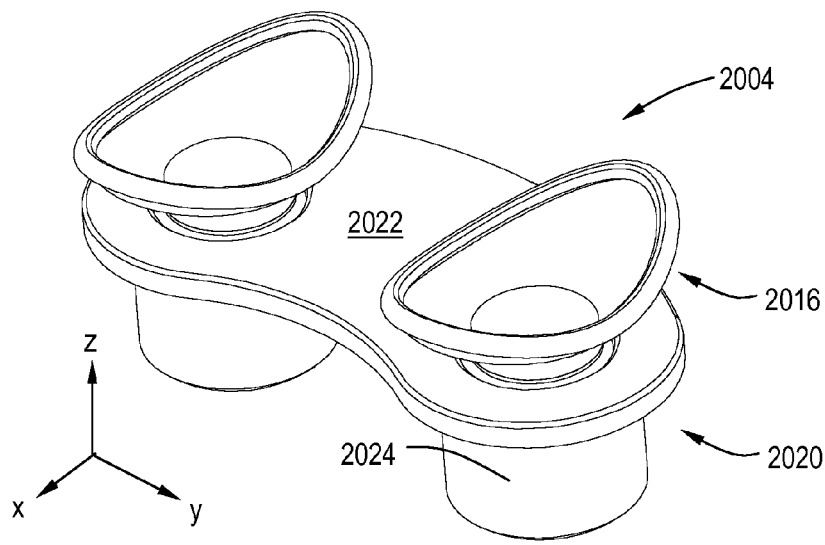
FIG. 42 is a perspective view of a tibial assembly of the joint of FIG. 39.
Figure 43:
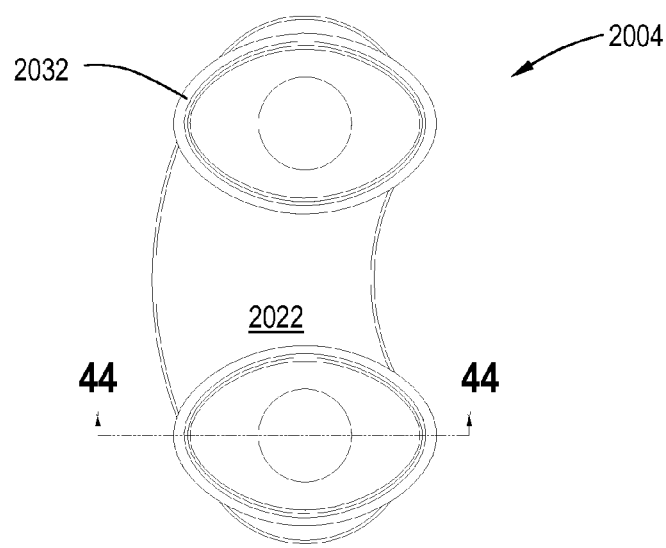
FIG. 43 is a top view of the tibial assembly of FIG. 42.
Figure 44:
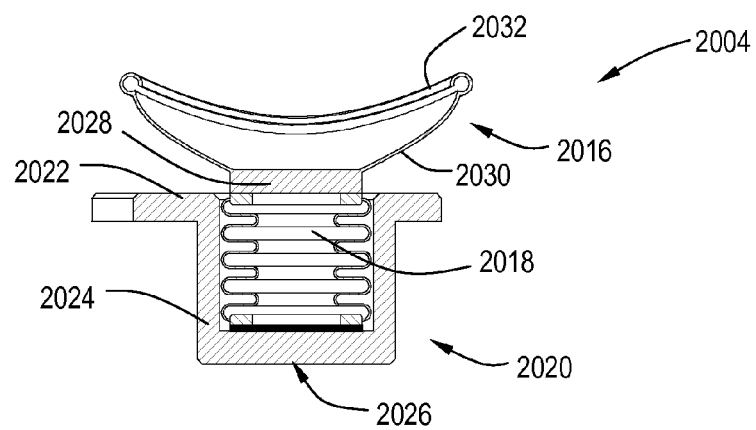
FIG. 44 is a view taken along lines 44-44 of FIG. 43.
Figure 45:
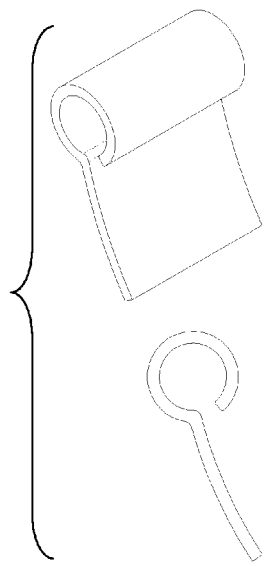
FIG. 45 is a perspective and sectional view of a first rim cross-sectional shape.
Figure 46:
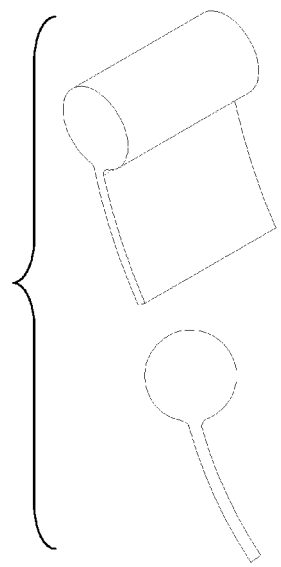
FIG. 46 is a perspective and sectional view of a second rim cross-sectional shape.
Figure 47:
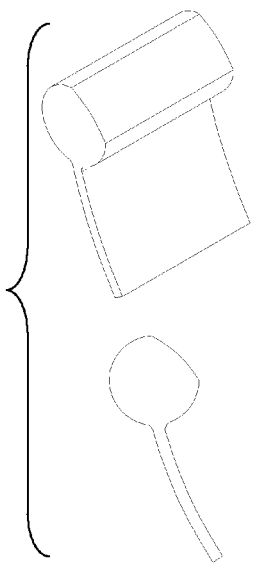
FIG. 47 is a perspective and sectional view of a third rim cross-sectional shape.

The tibial assembly 2004 is shown in more detail in FIGS. 42-44. It includes cups 2016, spring supports 2018, and a base 2020. The base 2020 is made from a rigid material and includes a generally flat plate 2022 with open-ended cylindrical receptacles 2024. Collectively the plate 2022 and the exterior of the receptacles 2024 define a mounting surface 2026. The mounting surface 2026 may be configured as an osseointegration surface, i.e. a surface designed to be infiltrated by bone growth to improve the connection between the implant and the bone. Osseointegration surfaces may be made from materials such as TRABECULAR METAL, textured metal, or sintered or extruded implant integration textures, as described above. The mounting surface 2026 and the receptacles 2024 are intended to be rigidly mounted to the upper end of a patient's tibia (not shown) and are sized and shaped for that purpose. The base 2020 may be mounted to a tibia using a press fit in a known manner, or partially or fully cemented to the tibia in a known manner.

Each cup 2016 is made from a rigid material (as described above) and includes a central disk 2028, a concave body 2030 extending upwards from the disk 2028, and a rim 2032 extending around the open periphery of the body 2030. The rim 2032 protrudes laterally away from (i.e. inboard and outboard) from the body 2028 and thus may be described as being substantially "thicker" or "wider" than the body 2030. The rim 2032 has a saddle-like or "ribbon" shape which is generally oval in plan view. As used herein, the term "oval" refers to a shape which has an overall length along one axis of symmetry (e.g. the x-axis seen in FIG. 42) that is substantially longer than an overall length along a second, perpendicular axis of symmetry (e.g. the y-axis seen in FIG. 42). In side elevation view, the saddle-like shape is "lowest" in the middle (relative to the central disk 2028) and curved upward at the ends. It is noted that the saddle-like shape may be oriented in any direction relative to the z-axis. That is, the "lowest" portion of the saddle-like shape could face in medial, lateral, anterior, or posterior directions. In the illustrated example there is one cup 2016 for each ridge 2014, however the tibial assembly 2004 could be modified to include more than one cup 2016 for each ridge 2014.

Figure 48:
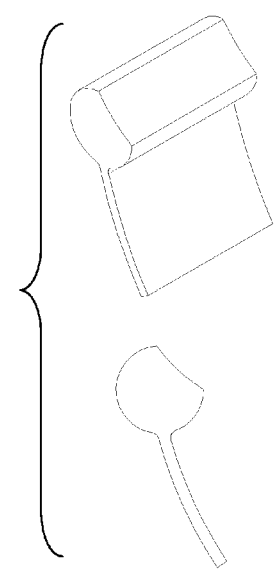
FIG. 48 is a perspective and sectional view of a fourth rim cross-sectional shape.

In the example shown in FIGS. 39-44, the rim 2032 is formed by a rolled, generally circular cross-sectional shape. The rim 2032 may take on a variety of shapes to adjust or "tune" its specific behavior in response to loading. Nonlimiting examples of potential cross-sectional shapes for the rim 2032 are shown in FIGS. 45 through 48 as follows: open circular (FIG. 45); solid circular (FIG. 46); solid generally circular with a convex bearing portion (FIG. 47); and solid generally circular with a concave bearing portion (FIG. 48).

The rim 2032 is wear-resistant, as that term is defined above. In the specific example illustrated, the rim 2032 includes a face layer (not separately indicated) of a known coating such as titanium nitride, chrome plating, carbon thin films, and/or diamond-like carbon coatings, and/or a another wear-resistant material such as ultra-high molecular weight (UHMW) polyurethane. This face layer is used to impart wear resistance, and may be extraordinarily thin. In this particular example, its as-applied thickness is about 0.0041 mm (0.00016 in.), or 160 millionths of a inch thick. The face layer is applied at a substantially uniform thickness over the surface over the rim 2032.

Each cup 2016 is connected to the base 2020 by one of the spring supports 2018. The spring supports 2018 are received in the receptacles 2024 and may be connected to the cups 2016 and the base 2020 by means such as welding or brazing, mechanical fasteners, or adhesives. The spring supports 2018 are configured to be substantially resistant to torsion (that is, rotation of the cup 2016 about the z-axis as shown in FIG. 42), but to permit controlled pivoting of the cup 2016 about the x- and y-axes so as to conform to the femoral component 2002, as described in more detail below. The spring supports 2018 are also substantially resistant to compression in the z-direction, having a very high effective spring rate. As used to describe the characteristics of the spring supports 2018, the term "substantially resistant" implies a spring rate or modulus sufficiently high so as to permit no significant deflection under normally-expected applied loads.

Figure 49:
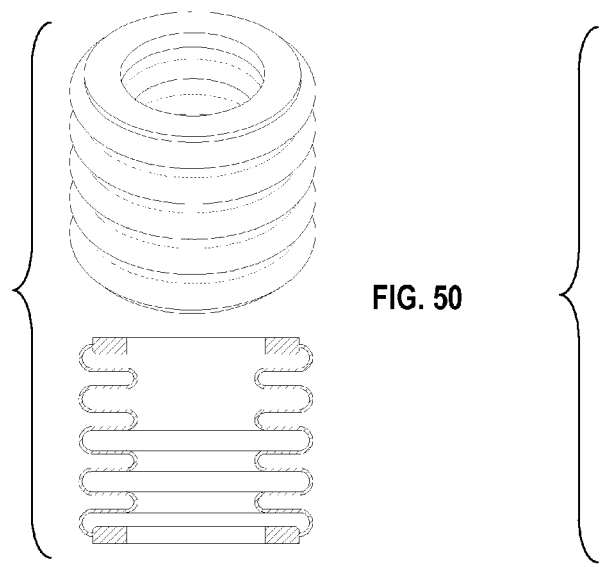
FIG. 49 is a perspective and sectional view of a first spring support configuration.
Figure 50:
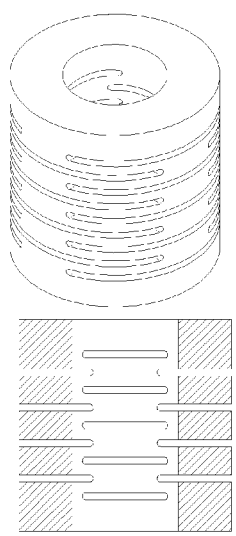
FIG. 50 is a perspective and sectional view of a second spring support configuration.
Figure 51:
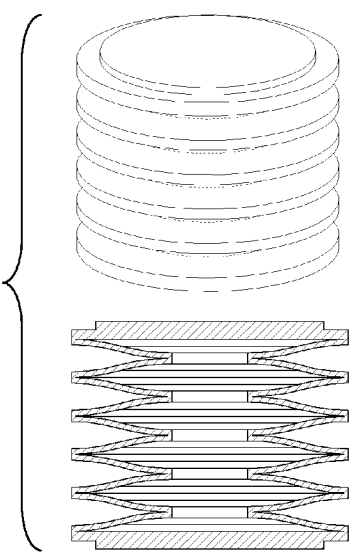
FIG. 51 is a perspective and sectional view of a third spring support configuration.

Various types of structures may be used for the spring supports 2018. In the example shown in FIGS. 39-44, and also in FIG. 49, the spring support 2018 is a bellows-like structure formed from sheet metal, with an annular wall having a plurality of convolutions. Other potential examples are a monolithic cylindrical structure with a plurality of slots selectively cut or otherwise formed therein, shown in FIG. 50, or a structure formed from a stack of conical spring washers (commonly known as "Belleville washers"), shown in FIG. 51. The material properties and overall dimensions of the spring support 2018 as well as details such as the number of slots, convolutions, or washers, may be varied to provide the spring characteristics needed for a particular application.

Figure 39:
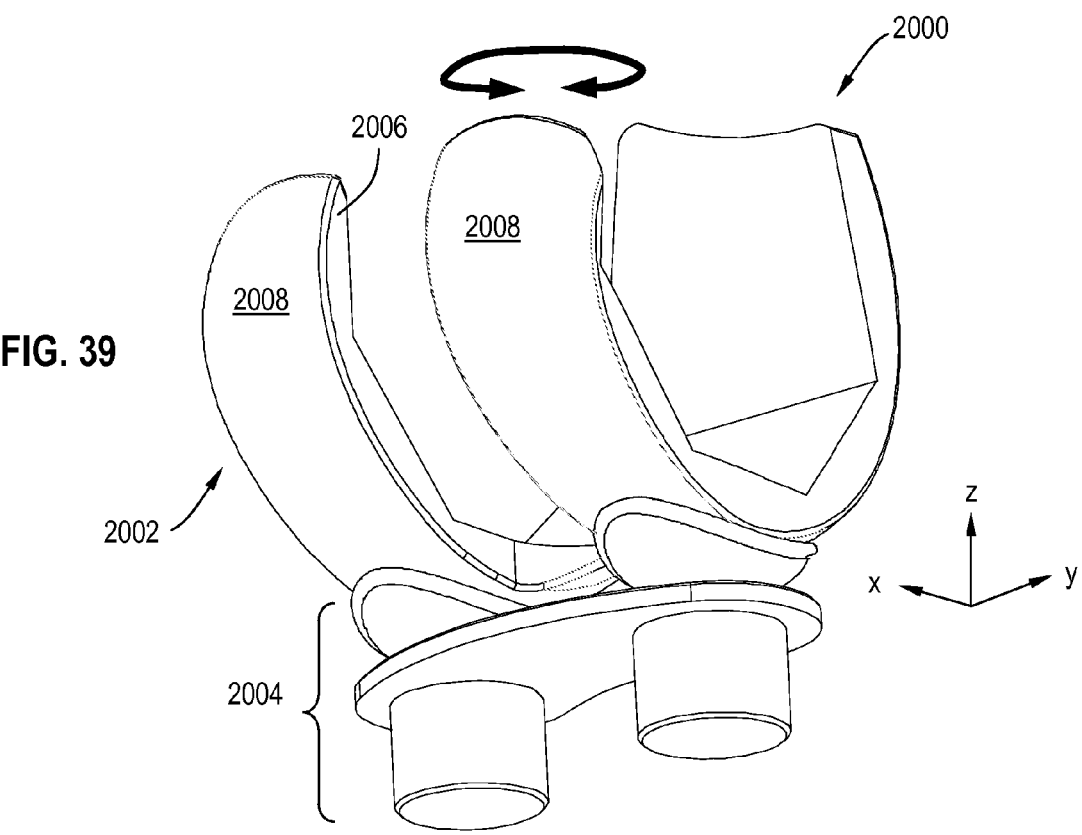
FIG. 39 is a perspective view of a prosthetic knee joint.
Figure 40:
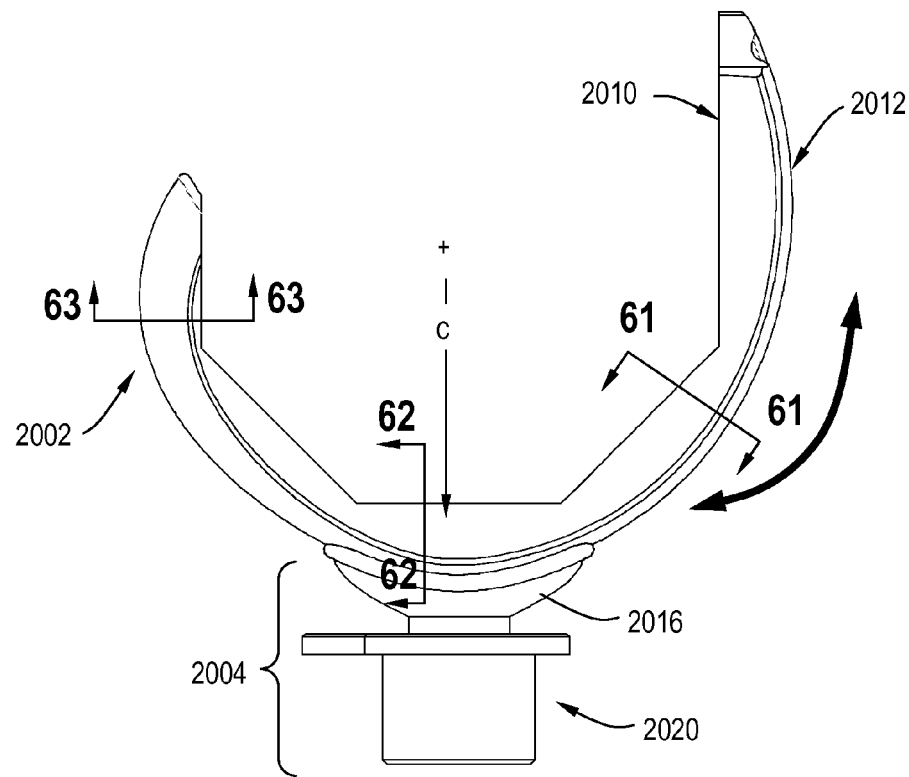
FIG. 40 is a side elevational view of the joint of FIG. 39.
Figure 41:
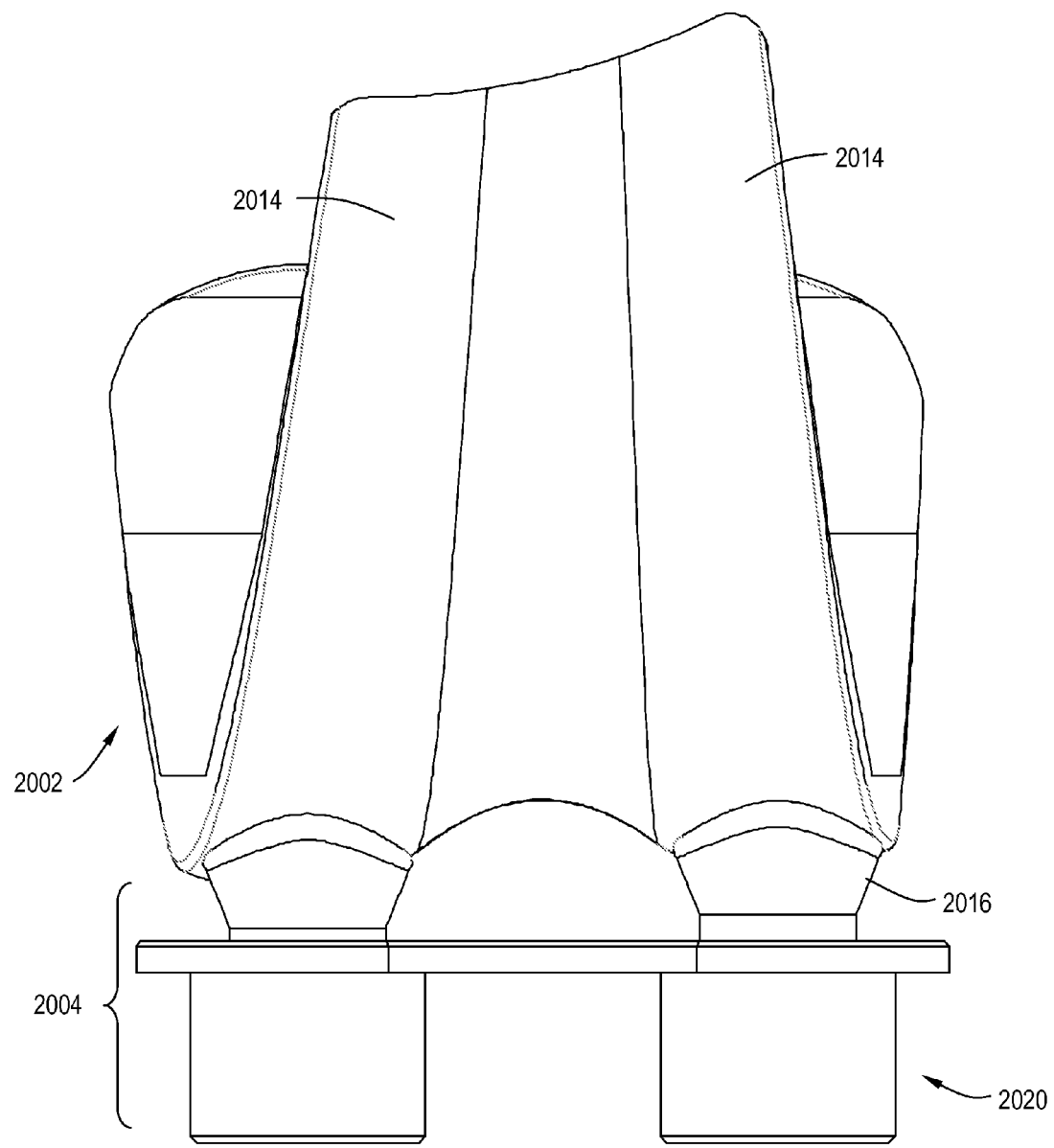
FIG. 41 is a rear elevational view of the joint of FIG. 39.

When assembled as shown in FIGS. 39-41, each of the rims 2032 bears against one of the ridges 2014. The spring supports 2018 elastically deflect and permit the cups 2016 to tilt (i.e. pivot about the x- and y-axes) so that the rims 2032 can engage the ridges 2014 at a appropriate angle. The joint 2000 permits flexion and extension movements (generally indicated by the heavy arrow in FIG. 40) by sliding of the ridges 2014 relative to the rims 2032. The joint 2000 also accommodates slight relative rotation of the femoral component 2002 and the tibial assembly 2004 about the z-axis (generally indicated by the heavy arrow in FIG. 39). This motion is accommodated through differential pivoting of the spring supports 2018 (i.e. positive pivoting of one spring support 2018 about the y-axis and negative pivoting of the other spring support 2018 about the y-axis).

FIGS. 52-54 depict an alternative tibial assembly 2104 for use with the femoral component 2002. It is similar to the tibial assembly 2004 described above and includes cups 2116, spring supports 2118, and a base 2120. The base 2120 is made from a rigid material and includes a generally flat plate 2122 with open-ended cylindrical receptacles 2124. The receptacles 2124 are significantly shallower than the receptacles 2024 described above, and house spring supports 2118 which are correspondingly shorter than the spring supports 2018 shown in FIGS. 42-44. A pin 2125 extends downward from the bottom of each receptacle 2124. It is noted that, depending on the particular application, the receptacles 2124 may be completely eliminated, with the spring support 2118 extending between a top surface of the plate 2122 and the cup 2116 (i.e. partially or fully taking the place of the central disk 2028 described above). Collectively the plate 2122 and the exterior of the receptacles 2124 and pins 2125 define a mounting surface 2126. The mounting surface 2126 may be configured as an osseointegration surface, i.e. a surface designed to be infiltrated by bone growth to improve the connection between the implant and the bone. Osseointegration surfaces may be made from materials such as TRABECULAR METAL, textured metal, or sintered or extruded implant integration textures, as described above. The base 2220 may be mounted to a tibia using a press fit in a known manner, or partially or fully cemented to the tibia in a known manner.

Figure 60:
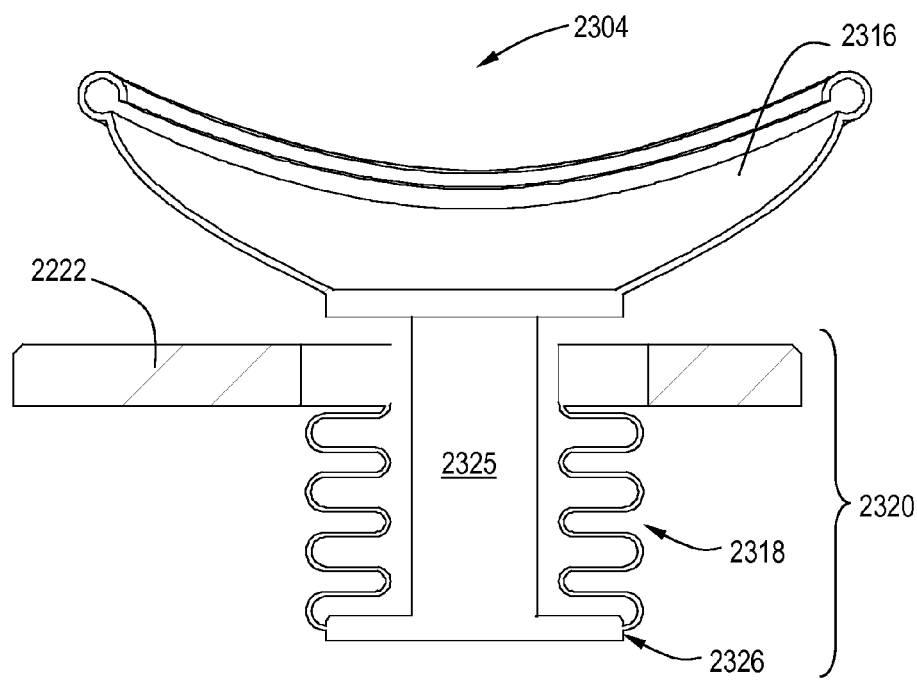
FIG. 60 is a cross-sectional view of an alternative tibial assembly.

FIG. 60 depicts an alternative tibial assembly 2304 for use with the femoral component 2002. It includes cups 2316 mounted to a base 2320. The base 2320 is made from a rigid material and includes a generally flat plate 2322. Each spring support 2318 is integral to the plate 2322 and comprises a bellows-like structure formed from sheet metal, with an annular wall having a plurality of convolutions. A central stem 2325 extends upward from the hollow center of each spring support 2318 to hold the corresponding cup 2316. Collectively the plate 2322 and the exterior of the spring elements 2318 define a mounting surface 2326 as described above.

FIGS. 55-57 depict yet another an alternative tibial assembly 2204 for use with the femoral component 2002. It includes cups 2216 mounted to a base 2220. The base 2220 is made from a rigid material and includes a generally flat plate 2222 with one or more pins 2225 extending downward from a lower surface thereof. Collectively the plate 2222 and the exterior of pins 2225 define a mounting surface 2226. The mounting surface 2226 may be configured as an osseointegration surface, i.e. a surface designed to be infiltrated by bone growth to improve the connection between the implant and the bone. Osseointegration surfaces may be made from materials such as TRABECULAR METAL, textured metal, or sintered or extruded implant integration textures, as described above. The base 2220 may be mounted to a tibia using a press fit in a known manner, or partially or fully cemented to the tibia in a known manner.

In this tibial assembly 2204, the spring support forms an integral part of each cup 2216. In particular, the walls of the cup 2216 are shaped with one or more discrete elastically deflectable curved portions 2217 (such as "S" or "C" curves) so as to permit the controlled pivoting motion described above with respect to the spring supports 2018.

Figure 58:
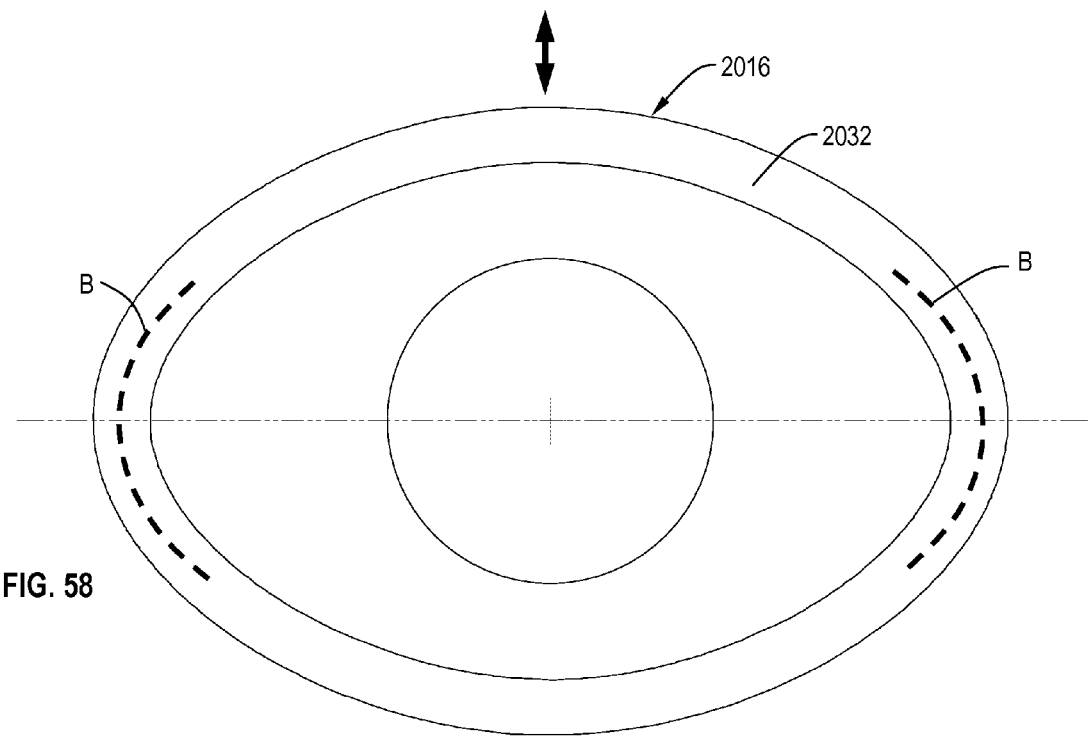
FIG. 58 is a top plan view of a cup of the joint of FIG. 39.

Nominally, when the joint 2000 is assembled and placed under load, each rim 2032 tends to define two separate "contact bands" with the opposed ridge 2014. Exemplary contact bands "B" are shown schematically in FIG. 58. Depending on the specific dimensions and curvatures of the femoral member 2002 and the cups 2016, the bands B may be a different size than depicted, or merge into a single complete annular contact band. As the joint 2000 is loaded, downward deflection of the rim 2032 is opposed by the elasticity of the rims 2032 in bending, as well as the hoop stresses in the rims 2032.

Figure 59:
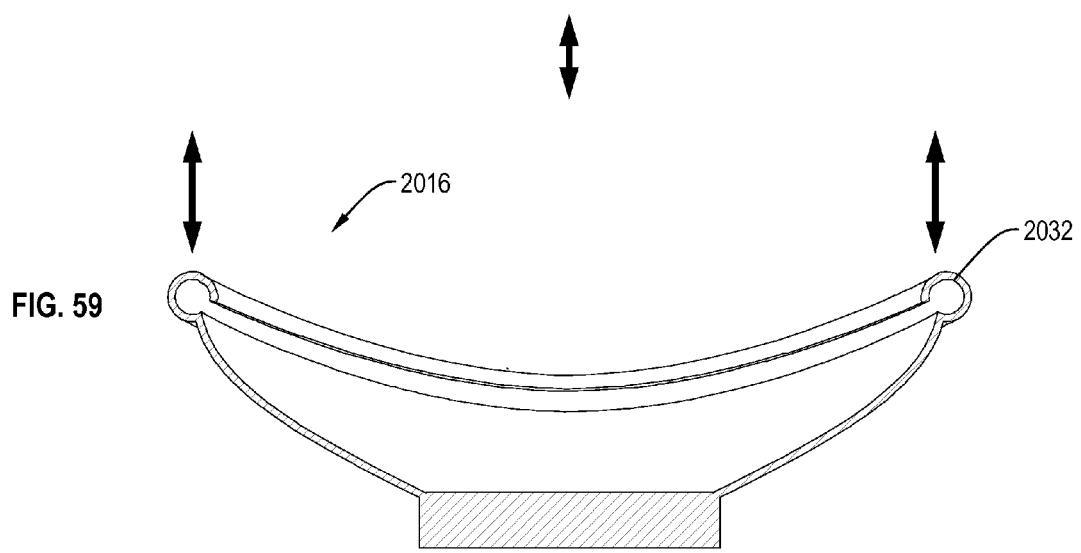
FIG. 59 is a cross-sectional view of the cup of FIG. 58.

The deflection properties of the rims 2032 are further controlled by their three-dimensional "saddle" shape. Each rim 2032 can be conceived of as a "ribbon" in space which has its own bending and torsional rigidity, separate from the support provided by the cup 2016. As a result, vertical deflection (i.e. along the z-axis) of the rim 2032, shown schematically by the heavy arrows in FIG. 59, results in a linked horizontal deflection (i.e. along the y-axis), shown schematically by the heavy arrows in FIG. 58. In other words, loading or unloading of the rim 2032 tends to cause expansion or contraction of the rim 2032 in plan view. This property tends to make the contact bands B remain tangent to the femoral contact surface 2012 at all times. This function is important in making the contract bands B remain at a stable position on the surface of the rim 2032, resulting in very low wear and long life.

Figure 61:
FIG. 61 is a cross-sectional view along lines 61-61 of FIG. 40.
Figure 62:
FIG. 62 is a cross-sectional view along lines 62-62 of FIG. 40.
Figure 63:
FIG. 63 is a cross-sectional view along lines 63-63 of FIG. 40.

Further control of the deflection properties of the rims 2032 may be exercised through the interaction of the curvatures of the ridges 2014 and the rims 2032. In particular, the curvature or width of the ridges 2014 parallel to the y-axis as shown in FIG. 39 may be varied. For example, FIGS. 61-63 show cross-sectional cuts taken through three different cutting planes depicted in FIG. 40. Explained another way, the ridges 2014 have variable lateral cross-sectional shapes at various locations along the arc length of the overall "U" curvature. Interaction of larger or smaller curvatures or widths of the ridges 2014 as the joint 2000 moves causes corresponding larger or smaller deflections in the rims 2032, in turn exerting control over the motion of the rims 2032 and further enhancing the ability to make the contact bands B remain tangent to the femoral contact surface 2012 at all times.

Also, in practice it is impossible to achieve surface profiles completely free of minor imperfections and variations. If the ridge 2014 and rim 2032 were both completely rigid, this would cause high Hertzian contact stresses (i.e. non-uniform contact) and rapid wear. Accordingly, an important feature of the illustrated joint 2000 is that the rims 2032 are conformable to the ridges 2014 when the joint 2000 is placed under load. The rims 2032 can conform to the imperfect femoral contact surface 2012 and deflect in an irregular shape. In other words, in addition to any uniform deflection which may be present, the deflected shape of the rims 2032 can include one or more specific locations or portions that are deflected towards or away from the nominal free shape to a greater or lesser degree than the remainder of the rims 2032. To achieve this controlled deflection, the cups 2016 and rims 2032 are thin enough to permit bending under working loads, but not so thin as to allow material yield or fatigue cracking, or to exceed the endurance limit of the material. The deflection is opposed by the elasticity of the rims 2032 in bending, as well as the hoop stresses in the rims 2032.

As noted above, known coatings such as titanium nitride, chrome plating, carbon thin films, and/or diamond-like carbon coatings may be used to impart wear resistance or augment the wear resistance of any of the contact surfaces and/or contact rims described above. To the same end, it may be desirable to surface treat either or both interfaces of any of the above-described implants or joints with a laser, shot peen, burnishing, or water shock process, to impart residual compressive stresses and reduce wear. The benefit could be as much from surface annealing and microstructure and microfracture elimination as smoothing itself.

The foregoing has described prosthetic joints with wear-resistant properties and conformal geometries. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A prosthetic knee joint, comprising:
    (a) a femoral member comprising a rigid material and having a convex-curved, wear-resistant femoral contact surface, the femoral contact surface including two spaced-apart protruding ridges having a convex cross-sectional shape; and
    (b) a tibial assembly including:
        (i) two individual and independently spaced-apart cups, each cup having a body and a peripheral rim extending around an open periphery of the body, wherein the body and rim of each respective cup are formed from a rigid material, the rim being substantially thicker than the body and defining a wear-resistant cup contact surface, wherein the rim has a saddle-like shape which is lowest in the middle and curved upwards at the ends relative to the body;
        (ii) a rigid base; and
        (iii) two separate spaced-apart spring supports, each spring support independently interconnecting at least part of a respective cup to the base, wherein each spring support is elastically deflectable so as to permit controlled pivoting motion of the respective cup relative to the base;
    (c) wherein each of the cup contact surfaces receives and bears directly against one of the protruding ridges of the femoral contact surface, so as to transfer axial and lateral loads between the tibial assembly and the femoral member, while allowing pivoting motion between the tibial assembly and the femoral member.

2. The prosthetic knee joint of claim 1, wherein each cup has a plan shape which is generally oval, having an overall length along one axis of symmetry which is substantially longer than an overall length along a second axis of symmetry perpendicular to the first axis of symmetry.

3. The prosthetic knee joint of claim 1 wherein each cup is shaped and sized so as to allow its rim to deform elastically and permit the cup contact surface to conform in an irregular shape to the femoral contact surface, when the knee joint is placed under a predetermined load.

4. The prosthetic knee joint of claim 1 wherein each spring support comprises a monolithic cylindrical structure with a plurality of slots formed therein.

5. The prosthetic knee joint of claim 1 wherein each spring support comprises at least one conical spring washer.

6. The prosthetic knee joint of claim 1 wherein each spring support comprises a generally cylindrical structure having an annular wall with a plurality of convolutions formed therein.

7. The prosthetic knee joint of claim 1 wherein each spring support is received within a receptacle formed in the base.

8. The prosthetic knee joint of claim 1 wherein each spring support comprises at least one discrete elastically deflectable curved portion included in the body of each cup.

9. The prosthetic knee joint of claim 1, wherein all of the contact surfaces are ceramic, metallic, or a combination thereof.

10. The prosthetic knee joint of claim 1, where each cup is sized so as to permit elastic deflection of the cup while limiting stresses in the cup to less than the endurance limit of the material, when a predetermined external axial load is applied to the joint.

11. The prosthetic joint of claim 1 wherein at least one of the contact surfaces includes a wear-resistant thin film or coating.

12. The prosthetic joint of claim 1 wherein each spring support comprises a generally cylindrical structure having an annular wall with a plurality of convolutions formed therein, and a central stem extending upwards through a center of the annular wall to connect to the respective cup.

13. The prosthetic joint of claim 1 wherein each ridge has variable lateral cross-sectional curvatures at spaced-apart locations along an arc length of each ridge.

* * * * *